US011499154B2

(12) United States Patent
Buj Bello

(10) Patent No.: US 11,499,154 B2
(45) Date of Patent: Nov. 15, 2022

(54) ANTISENSE TARGETING DYNAMIN 2 AND USE FOR THE TREATMENT OF CENTRONUCLEAR MYOPATHIES AND NEUROPATHIES

(71) Applicants: GENETHON, Evry (FR); UNIVERSITE D'EVRY-VAL-D'ESSONNE, Evry (FR); INSERM (INSTITUT NATIONAL DE LA SANTE ET DE LA RECHERCHE MEDICALE), Paris (FR)

(72) Inventor: Ana Maria Buj Bello, Paris (FR)

(73) Assignees: GENETHON, Evry (FR); UNIVERSITE D'EVRY-VAL-D'ESSONNE, Evry (FR); INSERM (INSTITUT NATIONAL DE LA SANTE ET DE LA RECHERCHE MEDICALE), Paris (FR)

( * ) Notice: Subject to any disclaimer, the term of this patent is extended or adjusted under 35 U.S.C. 154(b) by 522 days.

(21) Appl. No.: 16/604,121

(22) PCT Filed: Apr. 10, 2018

(86) PCT No.: PCT/EP2018/059208
§ 371 (c)(1),
(2) Date: Oct. 9, 2019

(87) PCT Pub. No.: WO2018/189208
PCT Pub. Date: Oct. 18, 2018

(65) Prior Publication Data
US 2021/0095291 A1    Apr. 1, 2021

(30) Foreign Application Priority Data

Apr. 10, 2017  (EP) .................................... 17305431

(51) Int. Cl.
| C12N 15/113 | (2010.01) |
| A61P 25/02 | (2006.01) |
| A61K 31/712 | (2006.01) |
| A61K 38/46 | (2006.01) |

(52) U.S. Cl.
CPC ........ *C12N 15/1137* (2013.01); *A61K 31/712* (2013.01); *A61K 38/465* (2013.01); *A61P 25/02* (2018.01); *C12N 2310/11* (2013.01); *C12N 2310/3233* (2013.01); *C12N 2320/31* (2013.01)

(58) Field of Classification Search
None
See application file for complete search history.

(56) References Cited

U.S. PATENT DOCUMENTS

| 6,156,303 A | 12/2000 | Russell et al. |
| 7,282,199 B2 | 10/2007 | Gao et al. |
| 2015/0258215 A1 | 9/2015 | Childers et al. |
| 2016/0058890 A1* | 3/2016 | Buj Bello ............ A61K 38/465 435/320.1 |

FOREIGN PATENT DOCUMENTS

| WO | WO 03/042397 A2 | 5/2003 |
| WO | WO 2005/033321 A2 | 4/2005 |
| WO | WO 2011/113889 A1 | 9/2011 |
| WO | WO 2015/055859 A1 | 4/2015 |
| WO | WO 2015/158924 A1 | 10/2015 |

OTHER PUBLICATIONS

Bitoun et al., "Mutations in dynamin 2 cause dominant centronuclear myopathy", Nature Genetics 37, 1207-1209 (2005).
Boisguerin et al., "Delivery of therapeutic oligonucleotides with cell penetrating peptides", Advanced Drug Delivery Reviews 87 (2015) 52-67.
Bolino et al., "Charcot-Marie-Tooth type 4B is caused by mutations in the gene encoding myotubularin-related protein-2", Nature Genetics 25(1):17-9 • Jun. 2000.
Chen et al., "Phenotype variability and histopathological Indings in patients with a novel DNM2 mutation", Neuropathology / vol. 38, Issue 1.
Cowling et al., "Increased Expression of Wild-Type or a Centronuclear Myopathy Mutant of Dynamin 2 in Skeletal Muscle of Adult Mice Leads to Structural Defects and Muscle Weakness", The American Journal of Pathology, vol. 178, No. 5, May 2011.
Cowling et al., "Reducing dynamin 2 expression rescues X-linked centronuclear myopathy", The Journal of Clinical Investigation, vol. 124, No. 3, Mar. 2014.
Daniele et al., "Antisense targeting of dynamin 2 by intramuscular delivery ofvivo-morpholinos rescues the pathology in a murine model of myotubular myopathy", Neuromuscular Disorders, vol. 27, p. 261, Oct. 2017 (Oct. 2017.
Ferguson et al., "Dynamin, a membrane-remodelling GTPase", Nat Rev Mol Cell Biol. Jan. 11, 2012;13(2):75-88.
Grimm et al., "The low abundance of U7 snRNA is partly determined by its Sm binding site", EMBO J. Mar. 1993;12(3):1229-38.
Hernandez et al., "Small Nuclear RNA Genes: a Model System to Study Fundamental Mechanisms of Transcription", The Journal of Biological Chemistry, vol. 276, No. 29, Issue of Jul. 20, pp. 26733-26736, 2001.
Jones et al., "Role of dynamin in the formation of transport vesicles from the trans-Golgi network", Science. Jan. 23, 1998;279(5350):573-7.

(Continued)

*Primary Examiner* — Tracy Vivlemore
(74) *Attorney, Agent, or Firm* — Knobbe, Martens, Olson & Bear LLP

(57) ABSTRACT

The present invention concerns the use of antisense oligonucleotides (AON) capable of inhibiting expression of dynamin 2, advantageously human dynamin 2, for use in the treatment of Charcot-Marie-Tooth disease (CMT) and centronuclear myopathies (CNM).

14 Claims, 6 Drawing Sheets

Specification includes a Sequence Listing.

(56) References Cited

OTHER PUBLICATIONS

Jungbluth et al., "Centronuclear (myotubular) myopathy", Orphanet J Rare Dis. Sep. 25, 2008;3:26.

Kojima et al., "Regulation of Bin1 SH3 domain binding by phosphoinositides", EMBO J. Nov. 10, 2004;23(22):4413-22. Epub Oct. 14, 2004.

Laporte et al., "A gene mutated in X-linked myotubular myopathy defines a new putative tyrosine phosphatase family conserved in yeast", Nat Genet. Jun. 1996;13(2):175-82.

Li et al., "Design and synthesis of dendritic molecular transporter that achieves efficient in vivo delivery of morpholino antisense oligo", Bioconjugate Chemistry, vol. 19, No. 7, Jul. 1, 2008 (Jul. 1, 2008), pp. 1464-1470.

Marks et al., "GTPase activity of dynamin and resulting conformation change are essential for endocytosis", Nature. Mar. 8, 2001;410(6825):231-5.

Nicot et al., "Mutations in amphiphysin 2 (BIN1) disrupt interaction with dynamin 2 and cause autosomal recessive centronuclear myopathy", Nat Genet. Sep. 2007;39(9):1134-9. Epub Aug. 5, 2007.

Pareyson et al., "New developments in Charcot-Marie-Tooth neuropathy and related diseases", Curr Opin Neurol. Oct. 2017;30(5):471-480.

Romero et al., "Centronuclear myopathies: a widening concept", Neuromuscul Disord. Apr. 2010;20(4):223-8. doi: 10.1016/j.nmd. 2010.01.014. Epub Feb. 23, 2010.

Royer et al., "The myotubularin-amphiphysin 2 complex in membrane tabulation and centronuclear myopathies", EMBO Rep. Oct. 2013;14(10):907-15. doi: 10.1038/embor.2013.119. Epub Aug. 6, 2013.

Schmid et al., "Dynamin: functional design of a membrane fission catalyst", Annu Rev Cell Dev Biol. 2011;27:79-105.

Schumperli et al., "The special Sm core structure of the U7 snRNP: far-reaching significance of a small nuclear ribonucleoprotein", Cell Mol Life Sci. Oct. 2004;61(19-20):2560-70.

Sharma et al., "Stem-loop 4 of U1 snRNA is essential for splicing and interacts with the U2 snRNP-specific SF3A1 protein during spliceosome assembly", Genes Dev., 2014, vol. 28, No. 22, pp. 2518-2531.

Tanabe et al., "Dynamin 2 in Charcot-Marie-Tooth Disease", Acta Med. Okoyama, vol. 66, No. 3, 2012, pp. 183-190.

Tasfaout et al., "ASO-mediated Dnm2 knockdown prevents and reverts myotubular myopathy in mice", Neuromuscular Disorders, vol. 26, T.O.14, Oct. 2016 (Oct. 2016), pp. s209-s210.

Yokota et al., "Extensive and Prolonged Restoration of Dystrophin Expression with Vivo-Morpholino-Mediated Multiple Exon Skipping in Dystrophic Dogs", Nucleic Acid Therapeutics, vol. 22, No. 5, Oct. 2012 (Oct. 2012).

Zuchner et al., "Mutations in the pleckstrin homology domain of dynamin 2 cause dominant intermediate Charcot-Marie-Tooth disease", Nat Genet. Mar. 2005;37(3):289-94.

International Search Report in application No. PCT/EP2018/059208, dated Jun. 29, 2018.

* cited by examiner

A/

B/

A/

B/

ANTISENSE TARGETING DYNAMIN 2 AND USE FOR THE TREATMENT OF CENTRONUCLEAR MYOPATHIES AND NEUROPATHIES

CROSS-REFERENCE TO RELATED APPLICATIONS

This application is the U.S. National Phase under 35 U.S.C. § 371 of International Application PCT/EP2018/059208, filed Apr. 10, 2018, which claims the benefit of European Application No. 17305431.3, filed Apr. 10, 2017, the disclosures of which are incorporated by reference herein in their entireties.

REFERENCE TO SEQUENCE LISTING

A sequence listing submitted as an ASCII text file via EFS-Web is hereby incorporated by reference in accordance with 35 U.S.C. § 1.52(e). The name of the ASCII text file for the Sequence Listing is LAUR006.002APC.txt, the date of creation of the ASCII text file is Oct. 2, 2019, and the size of the ASCII text file is 9 KB.

TECHNICAL FIELD

The present invention concerns antisense oligonucleotides (AON) which target the dynamin 2 gene and their use for the treatment of centronuclear myopathies (CNM), particularly myotubular myopathy (XLMTM), and Charcot-Marie-Tooth disease (CMT).

STATE OF THE ART

The centronuclear myopathies (CNM) belong to the group of congenital myopathies characterised by the central position of the nuclei in hypotrophic skeletal muscle fibres (reduced size present from birth). They are rare inherited diseases classified into three forms depending on their type of genetic transmission: the autosomal dominant form (AD CNM; OMIM 160150), the autosomal recessive form (AR CNM; OMIM 255200) and the X-linked recessive form or myotubular myopathy (XLCNM or XLMTM; OMIM 310400) (Romero, 2010; Jungbluth et al., 2008).

The autosomal dominant form of CNM accounts for almost 50% of cases of CNM (Romero, 2010). It has a wide phenotypic spectrum and the disease presents with severe to moderate forms. Patients exhibit generalised muscle weakness and reduced tone with delayed motor development and their muscle fibres exhibit the typical features of centronuclear myopathies, with one specific feature, the radial distribution of sarcoplasmic "strands" (Romero, 2010; Jungbluth et al., 2008).

This form of the disease is due to mutations in one of the alleles of the DNM2 gene, the gene coding for dynamin 2, a GTPase involved in membrane fission, endocytosis, transport, actin assembly and centrosome cohesion (Bitoun et al., 2005). Despite its ubiquitous expression, when mutated, dynamin 2 causes specific problems in skeletal muscle tissue or in peripheral nerves. Remarkably, some mutations of the dynamin 2 gene are also responsible for Charcot-Marie-Tooth disease (Züchner et al., 2005). Charcot-Marie-Tooth disease (CMT), also known as hereditary motor and sensory neuropathy, represents a heterogeneous group of neuropathies that has been historically divided into predominantly demyelinating (CMT1) and axonal (CMT2) forms, but intermediate forms have also been described. The overall prevalence of CMT is estimated 10-28/100 000, with more than 80 associated genes (Pareyson et al., 2017). Mutations in the DNM2 gene are currently linked to dominant intermediate (DI-CMTB) and axonal CMT (CMT2M) neuropathy with mild to moderate phenotype (Züchner et al., 2005; Züchner and Tao, 2015; Chen et al., 2018).

The autosomal recessive form of CNM may present with moderate to severe phenotypes and only accounts for a few cases. It has the typical features of the centronuclear myopathies (Romero, 2010; Jungbluth et al., 2008).

This form of the disease is due to mutations in the BIN1 (bridgingintegrator-1) gene which codes for amphyphysin 2, a protein which exists in around ten isoforms expressed in muscle or other tissues. It is involved in endocytosis, membrane recycling and cytoskeletal regulation. Muscle-specific amphyphysin 2 has an amphipathic helix in the N-terminal position which enables the membrane to form a curve, a BAR domain for protein homodimerisation and maintenance of the curve, a phosphoinositide binding domain and an SH3 domain which binds particularly to dynamin 2 (Nicot et al., 2007; Jungbluth et al., 2008).

The X-linked recessive form of the disease is the most severe of the CNM and in general affects boys, with a prevalence of one in 50,000 newborns. Antenatal signs are seen such as polyhydramnios (an excess of amniotic fluid during pregnancy) and reduced foetal movements. Patients develop respiratory failure, hypotonia and generalised muscle weakness and have a poor prognosis as approximately half die during the first year of life, usually because of respiratory failure. Less severely affected patients may survive into childhood or adolescence with the assistance of ventilation and feeding through a gastric tube (Romero et al., 2010; Jungbluth et al., 2008).

Histologically, nuclear internalisation, reduced skeletal muscle fibre hypotrophy and a predominance of type I fibres are seen. In many muscle fibres, the central nuclei are surrounded by a peripheral halo, representing reduced oxidative enzymatic activity and a reduction in the number of monofilaments, which is surrounded by a denser area made up of an accumulation of subsarcolemmal glycogen granules and mitochondrial aggregates. Because of their necklace shape around the fibre, the name "necklace" has been attributed to these fibres. Triads are less common and exhibit severe dysmorphism (a reduced number of T tubules in favour of longitudinal arrangement, irregularities in the position of the sarcoplasmic reticulum and swelling of the terminal cisterns) (Romero et al., 2010).

Myotubular myopathy is caused by mutations in the MTM1 gene, the gene coding for myotubularin (Laporte et al., 1996), an archetypal protein belonging to a family of fifteen homologous proteins called the MTMRs (Myotubularin-Related-Proteins). Myotubularin is a ubiquitous lipid phosphatase, the substrates of which are phosphatidylinositol-3-phosphate (PI3P) and phosphatidylinositol-3,5-bisphosphate (PI3,5P2), which it dephosphorylates into phosphatidylinositol (PI) and phosphatidylinositol-5-phosphate (PISP), respectively. These two substrates are second messengers located inside the endosomal membranes and play a role in intracellular vesicle transport. The mutations responsible for the disease are distributed throughout the coding sequence (Jungbluth et al., 2008). Remarkably, Bolino et al. (2000) have established that the neuropathy named Charcot-Marie-Tooth type 4B (CMT4B) is caused by mutations in the gene encoding the myotubularin-related protein-2 (MTMR2) for the form CMT4B1 or the myotubularin-related protein-13 (MTMR13) for the form CMT4B2.

Very interestingly, despite the phenotypic distinction between the three forms of CNM and the involvement of different genes, the diseases have identical histological features which suggest that common pathophysiological pathways may exist. Consistent with this idea, functional links have been identified between the three proteins involved: amphyphysin 2 is understood to bind to dynamin 2 (Kojima et al., 2004) and myotubularin (Royer et al., 2013), and all three proteins of common locations and partially similar functions, as they are found in the sarcolemma tubules and play a role in sarcolemmal organisation, membrane remodelling and intracellular vesicle transport. Furthermore, they all contain a specific phosphoinositide binding domain in their structure which strengthens the hypothesis of a link to membrane lipids.

Experiments in increasing dynamin 2 (or DNM2) expression in the skeletal muscle of adult mice have shown that excessive expression adversely affects muscle function and results in a fall in muscle force (Cowling et al., 2011). A recent study has shown excessive accumulation of dynamin 2 in mice and in patients suffering from myotubular myopathy (Cowling et al., 2014), suggesting that this protein may play a role in the disease. Consistent with this idea, crossing Mtm1-KO mice with $DNM2^{+/-}$ heterozygous mice reduces the expression of dynamin 2, improves the phenotype and prolongs lifespan in Mtm1-deficient mice (Cowling et al., 2014).

Based thereon, document WO 2015/055859 recommends the use of dynamin 2 inhibitors to treat centronuclear myopathies. In practice, proof of concept is provided on the one hand through the use of $DNM2^{+/-}$ and Mtm1-KO transgenic mice (model for XLMTM) and on the other hand through the use of DNM2+/− and $Bin1^{-/-}$ mice (model for AR CNM). In terms of the effectiveness of the inhibitors, only the shRNA against the murine Dnm2 gene has been tested. Antisense nucleotides, particularly those able to cause exon skipping, are mentioned amongst the alternative solutions. Two sequences SEQ ID NO 26 and 27 are disclosed, possibly in the form of U7snRNA, as being able to induce skipping of exons 2 and 8 of the human gene, respectively. SEQ ID NO: 26 is directed against the interior of exon 2, whereas SEQ ID NO: 27 does not match any region of the Dnm2 gene. In addition, no proof of efficacy or even feasibility is reported.

There is a clear need to provide new therapeutic solutions for the treatment of the centronuclear myopathies (CNM), but also of the neuropathies of the Charcot-Marie-Tooth disease (CMT) type.

SUMMARY OF THE INVENTION

Based on the assumption that an aberrant function of dynamin 2 in muscles and nerves is deleterious for these tissues, the present invention offers means for decreasing dynamin 2 expression levels which may be therapeutic for CNM patients but also for CMT patients carrying mutations in the DNM2 gene or in other genes resulting in increased levels of dynamin 2 protein.

In other words, the purpose of the present invention is to treat or improve forms of centronuclear myopathies (CNM) and Charcot-Marie-Tooth disease (CMT).

It further provides antisense oligonucleotides (AON) which appropriately reduce the level of expression of dynamin 2, chosen judiciously both in terms of the regions which they target and their form of administration.

Proof of the relevance of these AON has been reported both in vitro and in vivo, in terms of dynamin 2 production and the molecular histological, physical, physiological and functional characteristics of muscles treated using these AON. These antisense oligonucleotides therefore appear to be very promising clinical tools.

Definitions

The definitions below represent the meaning generally used in the context of the invention and should be taken into account unless another definition is explicitly stated.

In the frame of the invention, the articles "a" and "an" are used to refer to one or several (i.e., at least one) of the grammatical object of the article. By way of example, "an element" means at least one element, i.e. one or more than one elements.

The terms "around", "about" or "approximately" as used therein when referring to a measurable value such as an amount, a temporal duration and the like should be understood as encompassing variations of ±20% or ±10%, preferably ±5%, more preferably ±1%, and still more preferably ±0.1% from the specified value.

Intervals/ranges: throughout this disclosure, various aspects of the invention can be presented in the form of a value interval (range format). It should be understood that the description of values in the form of an interval is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

"Isolated" means altered or removed from its natural environment or state. For example, an isolated nucleic acid or peptide is a nucleic acid or peptide which has been extracted from the natural environment in which it is usually found whether this be in a plant or living animal for example. A nucleic acid or peptide for example which is naturally present in a living animal is not an isolated nucleic acid or peptide in the sense of the invention whereas the same nucleic acid or peptide partially or completely separated from other components present in its natural environment is itself "isolated" in the sense of the invention. An isolated nucleic acid or protein can exist in substantially purified form, or can exist in a non-native environment such as, for example, a host cell.

In the context of the present invention, the following abbreviations for the commonly occurring nucleic acid bases are used: "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The nucleotide sequence which codes for a protein or an RNA or cDNA may possibly contain introns.

The terms "encoding" or "coding for" refer to the inherent property of specific sequences of nucleotides in a polynucleotide, such as a gene, a cDNA or an mRNA, used as a matrix to produce other polymers and macromolecules in biological processes, having either a defined nucleotide sequence (for example rRNA, tRNA and mRNA), or a defined amino acid sequence and the biological properties resulting therefrom. A gene therefore codes for a protein if transcription and translation of the mRNA corresponding to this gene produces the protein in a cell or in another biological system. Both the coding strand, the nucleotide sequence of which is identical to the mRNA sequence and is usually provided in the sequence listings and databases, and the non-coding strand, used as the template for transcription of a gene or cDNA, may be referred to as coding for the protein or for other product of this gene or cDNA.

In genes of eukaryotic organisms, the "exons" are segments of an RNA precursor (pre-mRNA) which are preserved in the RNA after splicing and which are found in the mature RNA in the cytoplasm. Segments of the RNA precursor which are removed during splicing are on the other hand called "introns".

The term "polynucleotide" as used in the context of the invention is defined as a chain of nucleotides. In addition, nucleic acids are polymers of nucleotides. Thus, the terms nucleic acids and polynucleotides as used therein are interchangeable. It is well known in the field of molecular biology and genetic engineering that nucleic acids are polynucleotides which can be hydrolysed into the monomeric "nucleotides". Nucleotides can be hydrolysed into "nucleosides". As used in the context of the invention, polynucleotides include, but are not limited to all types of nucleic acid sequences, i.e. molecules of nucleic acids which can be obtained by any means available in the art, including recombinant methods, i.e. cloning of nucleic acid sequences from a recombinant library or a cell genome, using ordinary cloning technologies such as PCR or by synthesis.

As used therein, the term "oligonucleotide" designates a polynucleotide which preferentially does not exceed 100 nucleotides (or bases) in size or even 95, 80, 75, 70, 65, 60, 55 or even 50 nucleotides (or bases). In the context of the invention and advantageously, an oligonucleotide contains at least 5, 10, 15, 20, 25, 30, 35, 40, 45 or even 50 nucleotides (or bases).

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein or peptide sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The terms "identical" or "homologous" refer to the sequence similarity or sequence identity between two polypeptides or between two nucleic acid molecules. When a position in both of the two compared sequences is occupied by the same base or amino acid monomer subunit (for example when a position in each of the two DNA molecules is occupied by adenine), the molecules are then homologous or identical at that position. The percent of homology/identity between two sequences depends on the number of matching positions shared by the two sequences and represents this number divided by the number of positions compared, multiplied by 100. For example, if 6 of the 10 positions in two related sequences are identical, the two sequences are 60% identical. As a general rule, the comparison is made by aligning the two sequences in order to obtain maximum homology/identity.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

"Expression vector" refers to a vector comprising a recombinant polynucleotide comprising expression control sequences operatively linked to a nucleotide sequence to be expressed. An expression vector comprises in particular sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

The term "promotor" as used here is defined as a DNA sequence recognised by the cell synthesis machinery or introduced synthetic machinery, which is required to initiate specific transcription of a polynucleotide sequence.

As used herein, the term "promoter/regulatory sequence" means a nucleic acid sequence, which is required for expression of a gene product operably linked to the promoter/regulatory sequence. In some instances, this sequence may be the core promoter sequence and in other instances, this sequence may also include an enhancer sequence and other regulatory elements, which are required for expression of the gene product. The promoter/regulatory sequence may, for example, be one which expresses the gene product in a tissue specific manner.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics, which are normal or expected for one cell or tissue type, might be abnormal for a different cell or tissue type.

The terms "patient," "subject," "individual," and the like are used interchangeably herein, and refer to any animal, or cells thereof whether in vitro or in situ, amenable to the methods described herein. In certain non-limiting embodiments, the patient, subject or individual is an animal, preferably a mammal, more preferably a human. It may also be a mouse, a rat, a pig, dog or non-human primate (NHP), such as the macaque monkey.

In the sense of the invention, a "disease" or "pathology" is a state of health of an animal in which its homeostasis is adversely affected and which, if the disease is not treated, continues to deteriorate. Conversely, in the sense of the invention, a "disorder" is a state of health in which the animal is able to maintain homeostasis but in which the state of health of the animal is less favourable than it would be in the absence of the disorder. Left untreated, a disorder does not necessarily result in deterioration in the state of health of the animal over time.

A disease or disorder is "alleviated" ("reduced") or "ameliorated" ("improved") if the severity of a symptom of the disease or disorder, the frequency with which such a symptom is experienced by the subject, or both of these, is reduced. This also includes the disappearance of progression of the disease, i.e. halting progression of the disease or disorder. A disease or disorder is "cured" ("recovered") if the severity of a symptom of the disease or disorder, the frequency with which such a symptom is experienced by the patient, or both, is eliminated.

In the context of the invention, a "therapeutic" treatment is a treatment administered to a subject who displays the symptoms (signs) of pathology, with the purpose of reducing or removing these symptoms. As used herein, the "treatment of a disease or disorder" means reducing the frequency or severity of at least one sign or symptom of a disease or disorder experienced by the subject. A treatment is said to be prophylactic when it is administered to prevent the development, spread or worsening of a disease, particularly if the subject does not have or does not yet have the symptoms of the disease and/or for which the disease has not been diagnosed.

In the sense of the invention, an "effective quantity" or an "effective amount" of a compound is that amount of compound which is sufficient to provide a beneficial effect to the subject to which the compound is administered. The expression "therapeutically effective quantity" or "therapeutically effective amount" refers to a quantity which is sufficient or effective to prevent or treat (in other words delay or prevent the development, prevent the progression, inhibit, decrease or reverse) a disease or a disorder, including alleviating symptoms of this disease or disorder.

DETAILED DESCRIPTION OF THE INVENTION

According to a first aspect, the invention involves antisense oligonucleotides (AON) capable of inhibiting the expression of the dynamin 2 gene, more specifically capable of interfering with splicing or translation of the dynamin 2 gene, advantageously the human dynamin 2 gene.

In the context of the present application, the term "dynamin" (DNM) refers to GTPase proteins involved in membrane fission (Ferguson et al., 2012), endocytosis (Marks et al., 2001), and membrane traffic (Jones et al., 1998), assembly of actin (Ferguson et al., 2012) and centrosome cohesion (Bitoun et al., 2005). The dynamins contain an N-terminal domain carrying the GTPase activity, a central ("middle") domain enabling dimerisation of the protein, a PH ("Pleckstrin-Homology") domain promoting binding to phosphoinositides, a GED ("GTPase Effector Domain") domain and a PRD ("Proline-Rich Domain") involved in protein-protein interactions. Three dynamins have been identified in humans: dynamin 1, which is expressed exclusively in neurons, dynamin 3, which is expressed mainly in the brain and testes, and dynamin 2 (DNM2), which is expressed ubiquitously.

The present invention is intended more specifically for dynamin 2. It may be the murine dynamin 2 gene (uc029wxt.1), the mRNA sequence of which is accessible in the NCBI database, under reference NM 001253893. Advantageously, it is the human dynamin 2. Dynamin 2 is encoded by the Dnm2 or DNM2 gene (Gene ID 1785). More specifically, the Dnm2 gene is located on chromosome 19, the sequence of which (120 825 base pairs) is accessible in the NCBI database under reference NG 008792.1 and the mRNA sequence under number NM 001005360.2. It should be noted that the dynamin 2 gene and the products of this gene also carry other names such as DYN2, DYN2 HUMAN, dynamin II, DYNII and/or are involved in diseases such as CMTDI1, CMTDIB, DI-CMTB.

In the context of the present application, the terms "inhibit dynamin 2" or "inhibit the expression of the dynamin 2 gene" refers to the capacity of a molecule, i.e. an antisense oligonucleotide, to decrease, reduce or even block expression of dynamin 2 and/or decrease, reduce or even block the production of an active functional dynamin 2. In the present case, this involves direct inhibition, the antisense oligonucleotide binding directly to the nucleic acid coding for dynamin 2 or to a part thereof. According to a specific embodiment, the antisense oligonucleotide according to the invention binds to the pre-messenger RNA or the messenger RNA of dynamin 2.

According to the invention, the antisense oligonucleotide inhibits, reduces or decreases the expression and/or activity of dynamin 2 by at least 10% or even by at least 30%, 40%, 50%, 60%, 70%, 75%, 80%, 85%, 90% or even 95%, advantageously both in vitro and in vivo. The level of expression of the protein may be quantified by any technique known in the art, such as by analysing the transcript level (particularly mRNA) using any appropriate technique such as quantitative PCR. Alternatively, the quantity of protein produced may be assessed for example using the Western blot technique (see FIGS. 1 and 2) or ELISA using a specific dynamin 2 antibody. The quantity of functional active protein produced may also be assessed measuring a characteristic activity of said protein, e.g. its GTPase activity.

According to a specific embodiment, the inhibition achieves a level of expression or activity of dynamin 2 between that of an affected subject (with overexpression of dynamin 2 and/or suffering from centronuclear myopathy or Charcot-Marie-Tooth disease) and that of a healthy subject (without overexpression of dynamin 2 and/or not suffering from centronuclear myopathy or Charcot-Marie-Tooth disease). According to a preferred embodiment, the inhibition may achieve a level of expression or activity of dynamin 2 equal to or even less than a normal level. As previous studies have shown that excessively drastic inhibition of dynamin 2 may have deleterious effects, inhibition advantageously produces a level of expression or activity of DNM2 of at least 5%, 10, 20, 30, 40 or even 50% of the so-called normal level, i.e. the level found in a healthy subject.

In the context of the invention, the term "antisense oligonucleotide" or AON refers to a sequence of nucleic acids (DNA, RNA or a chemical analogue) complementary to a messenger RNA (mRNA) or even a pre-messenger RNA (pre-mRNA) of a gene, able to bind to the gene and thereby interfering with its expression particularly in transcription, splicing, stability of the RNA or translation of the corresponding gene. In the context of this application, the terms "target", "hybridises with", "complementary to" and "directed against" are used equivalently.

As known in the art (see for example Boisguérin et al., Adv. Drug Deliv. Rev. 87, 52-67, 2015), an "antisense" or "antisense oligonucleotide" may be an interfering RNA, an antisense nucleic acid or a ribozyme.

The terms "interfering RNA" include in particular siRNA ("small interfering RNA"), miRNA ("micro RNA"), dsRNA ("double stranded RNA"), ssRNA ("single stranded RNA"), and shRNA ("small hairpin RNA").

The antisense nucleic acids in particular comprise the RNAse H-competent oligonucleotides and the splice switching oligonucleotides (SSO).

Preferentially, the antisense oligonucleotide according to the invention is capable of hybridising specifically to the gene or transcripts (particularly mRNA and pre-mRNA) coding for dynamin 2. In other words, the said oligonucleotide and the target sequence form under determined (moderate or advantageously strong) stringency conditions, a double-stranded molecule.

The stringency conditions depend conventionally on experimental conditions such as temperature, ionic force (concentration of salts) and concentrations of denaturing agents or organic solvents (such as formamide) in the reaction medium. These conditions and their possible variations are well known to the person skilled in the art. Typical stringency hybridisation conditions include temperatures above 30° C., preferentially above 35° C., preferentially still above 42° C. and/or a salinity under 500 nM, advantageously under 200 nM. An example of high stringency conditions includes in particular hybridisations and washings performed using compositions containing sodium chloride (0.015 M) and sodium citrate (0.0015 M) at 65-68° C. (See Sambrook, Fritsch & Maniatis, Molecular Cloning. A Laboratory Manual, 2nd Ed, Cold Spring Harbor Laboratory, N Y 1989). More moderate stringency conditions may correspond to hybridisations and washings conducted in the same compositions but at a lower temperature, typically between 50 and 65° C.

To achieve this hybridisation, the antisense oligonucleotide must have sufficient identity with the target sequence to enable the two strands to pair with each other. This is achieved when the two sequences are identical but may also occur in the presence of one or more (in particular 2, 3, 4 or 5) divergent nucleotides, advantageously when they are located within the sequence. In other words, it is not necessary for antisense oligonucleotide according to the invention to be 100% complementary to the sequence which it targets in order to specifically hybridise to it. Therefore and preferentially, the antisense oligonucleotide according to the invention displays at least 60%, 65%, 70%, 75%, 80%, 85%, and advantageously 90%, 91%, 92%, 93%, 94%, 95%, 96%, 97%, 98%, 99%, even more advantageously 100% identity with the targeted sequence. In other words, the degree of complementarity between the antisense oligonucleotide according to the invention and the sequence which it targets is advantageously greater or equal to 90%, 91%, 92%, 93%, 94%, 95%, 96%, 97%, 98%, 99%, or even more advantageously 100%.

In the context of the invention, "complementary" or "complementarity" refers to the capacity of a polynucleotide to form base pairs with another polynucleotide molecule. The base pairs typically develop through hydrogen bonds between the nucleotides and those of the antiparallel strand (typically A with T or U and C with G), thereby forming a duplex. In a manner known to the person of the art, when reference is made to a RNA and in contrast to DNA, the base which pairs with the adenosine (A) is uracil (U) and not thymidine (T). However, and in the frame of the present application, the use of the symbol T implies that it may include a U. In practice, perfect complementarity or a 100% degree of complementarity refers to the situation in which each nucleotide of a strand binds to a nucleotide of the other strand. Conversely, complementarity of under 100% indicates that some, but not all, nucleotides of the two strands may pair because of non-complementary bases or differences in length between sequences. It should be noted that mismatch(es) may be located at the extremities of the sequences or inside the sequences themselves. In case of several mismatches, the unpaired bases may be contiguous or isolated.

As already stated, the present invention discloses antisense nucleic acids capable of inhibiting the expression of dynamin 2. In the context of the present application, the expression "antisense oligonucleotide" (AON) is used consistent with a preferred embodiment of the invention which involves using nucleic acids of 50 nucleotides, or even 40 or 30 nucleotides, or even 25, 20, 15 or less or even 10 or fewer nucleotides. According to one specific embodiment, an AON according to the invention comprises 15, 16, 17, 18, 19, 20, 21, 22, 23, 24 or 25 nucleotides. Such an AON may be complementary to part or all of the sense nucleic acid coding for dynamin 2, for example complementary to the strand coding for the double stranded molecule of the complementary DNA (cDNA) or complementary to the messenger RNA (mRNA) sequence.

In practice, and in the context of the application, the AON sequence corresponds to the inverse complementary sequence to the dynamin 2 gene sequence, particularly dynamin 2 of human origin accessible in the NCBI database, reference NG 008792.1.

According to one specific embodiment, the AON is a DNA or RNA molecule capable of hybridising to the target pre-mRNA and/or mRNA coding for dynamin 2.

According to a first aspect, the AON of the invention inhibits the translation of the mRNA coding for dynamin 2. According to another aspect, the AON according to the invention targets the 5'UTR ("Untranslated Transcribed Region") of dynamin 2, i.e. the portion of mRNA located upstream of the start codon (ATG) or overlapping said start codon. By binding to this region, such an AON is liable to interfere with transcription and/or translation and therefore at least partially inactivate this gene. As a result and in the presence of an effective AON, the quantity of dynamin 2 produced is reduced.

According to one specific embodiment, the AON targets the proximal region of the translation start codon (ATG), advantageously targeting the region comprising the 100 nucleotides located upstream of the ATG, advantageously the region located between positions −25 and −90 with reference to the ATG and even more advantageously the region located between positions −49 and −70 with regard to the ATG. Without being bound to any theory, such an AON would block progression of the translation start complex on the start codon (ATG), preventing assembly of the ribosome.

According to a specific embodiment, such an AON comprises or consists of the sequence GACCCT-CAACGACCTGGCCCC (SEQ ID NO: 4) or a sequence having at least 90% identity to the sequence SEQ ID NO: 4. In practice and as an example, a 19 nucleotide AON devoid of the 2 bases at the 5' or 3' end (or 1 base at each end) of SEQ ID NO: 4 would still display 90% identity with this sequence and would therefore be concerned by the present invention.

According to another embodiment, the AON chosen targets and hybridises with the regions involved in the pre-mRNA splicing, particularly the acceptor sites (SA for "splice acceptor") and/or the ESE ("exon splicing enhancer") sequences and/or the branching points (BP). In the presence of such an AON, the splicing sites masked by the AON are "blocked" and are not recognised by the cell machinery. As a consequence, the targeted exon is not incorporated into the resultant messenger RNA which is therefore "skipped" thereby changing the exon composition of the mRNA. According to this embodiment, said "exon skipping" occurs at the splicing stage of the pre-messenger RNA (or pre-mRNA) of dynamin 2, defined as the translation product of the gene coding for the dynamin 2 protein obtained before splicing.

As such and by judiciously targeting certain exons, it is possible to produce a truncated and/or inactive protein through the introduction of stop codons and/or a change in the reading frames. Therefore and using this strategy, it is possible to reduce the protein level of dynamin 2.

With regard to dynamin 2 and as identified in the frame of the present application, the AON is preferentially chosen for its capacity to induce skipping of exon 2, exon 6 or exon 8 of the dynamin 2 gene.

According to one embodiment, the antisense oligonucleotide of the invention specifically enables or induces skipping of exon 8 on the dynamin 2 pre-mRNA. Advantageously, the said AON targets the junction between intron 7 and exon 8 on the dynamin 2 pre-mRNA. According to a specific embodiment, such an AON comprises or consists of the sequence CTGGACCATCCTATGAGGAAAAGGA (SEQ ID NO: 1) or a sequence exhibiting at least 90% identity or even 95%, 96%, 97%, 98% or even 99% identity with the sequence SEQ ID NO: 1. In practice and as an example, an 18 nucleotide AON devoid of 2 bases at the 5' or 3' extremities (or 1 base at each extremity) of SEQ ID NO: 1 would still exhibit 90% identity with this sequence and would therefore be concerned by the invention.

According to another embodiment, the antisense oligonucleotide of the invention specifically enables or induces skipping of exon 6 on the dynamin 2 pre-mRNA. Advantageously, the said AON targets the junction between exon 6 and intron 6 on the dynamin 2 pre-mRNA. According to a specific embodiment, such an AON comprises or consists of the sequence CGTGCAAACCCTTGCAGTACCTGAT (SEQ ID NO: 2) or a sequence exhibiting at least 90% identity or even 95%, 96%, 97%, 98% or even 99% identity with the sequence SEQ ID NO: 2. In practice and as an example, a 23 nucleotide AON devoid of 2 bases at the 5' or 3' extremities (or 1 base at each extremity) of SEQ ID NO: 2 would still exhibit over 90% identity with this sequence and would therefore be concerned by the invention.

According to another embodiment, the antisense oligonucleotide of the invention specifically enables or induces skipping of exon 2 on the dynamin 2 pre-mRNA. Advantageously, the said AON targets the junction between exon 2 and intron 2 on the dynamin 2 pre-mRNA. According to a specific embodiment, such an AON comprises or consists of the sequence TCAGGCCGCCCCATTTTACCTGTTT (SEQ ID NO: 3) or a sequence exhibiting at least 90% identity or at least 95%, 96%, 97%, 98% or even 99% identity with the sequence SEQ ID NO: 3. In practice and as an example, a 23 nucleotide AON devoid of 2 bases at the 5' or 3' extremity (or 1 base at each extremity) of SEQ ID NO: 3 would still exhibit over 90% identity with this sequence and would therefore be concerned by the invention.

As already stated, an antisense oligonucleotide according to the invention can have a size of about 5, 10, 15, 20, 25, 30, 35, 40, 45 or 50 nucleotides, advantageously between 15 and 25 nucleotides, and even more advantageously 20, 21, 22, 23, 24 or 25 nucleotides.

An antisense oligonucleotide according to the invention may be obtained by chemical synthesis and enzymatic ligation reactions according to procedures which are known in the technical domain. In particular, antisense RNA may be synthesised chemically produced by in vitro transcription from a linear matrix (such as PCR products) or circular matrix (such as viral or non-viral vectors) or produced by in vivo transcription from viral or non-viral vectors.

In practice, an oligonucleotide according to the invention may be synthetic or produced in situ using a genetic construction. It may be administered as it is or in the form of a precursor or a DNA molecule coding for it.

Antisense oligonucleotides may be chemically altered to increase their stability, resistance to nucleases, and specificity for their target and/or to have improved pharmacological properties.

In particular, for in vivo use, in order to avoid their degradation and/or increase the physical stability of the duplex formed between the antisense and the targeted sense nucleic acid, the AON may be stabilised via chemical modifications such as modifications of the phosphate backbone and chemical bonds between the nucleosides.

Therefore, and in a non-restrictive manner, the following different types of oligonucleotides can be used in relation to the present invention:

Methylphosphonate (MP);

Phosphotriester;

Phosphoroseleniate;

Phosphorothioate (PS);

2'-fluoro or 2'-O-alkyl oligomer, in particular 2'-O-methyl (2'-OMe);

2'-O-methyl Phosphorothioate (2'-OMePS);

Phosphorodiamidate morpholino (PMO);

Peptide Nucleic Acid (PNA);

tricyclo-DNAs.

AONs according to the invention, which may be chemically modified, may be administered in a naked form, or free, or using delivery systems which increase the stability and/or targeting, such as liposomes or incorporated into carriers such as hydrogels, cyclodextrins, biodegradable nanocapsules, bioadhesive microspheres, protein vectors or in combination with a cationic peptide.

Antisense oligonucleotides (AON) according to the invention may be administered using a transporter or carrier. Such a transporter may for example be a Cell Penetrating Peptide (CCP), advantageously in the form of a CPP-AON conjugate, possibly conjugated using a linker. Advantageously, this would consist of cationic peptides such as Poly-L-Lysine (PLL), oligo-arginine, Tat protein, Penetratin or Transportan peptides, and their derivatives (such as Pip).

In this context and by way of example, PPMO (Peptide phosphorodiamidate morpholino oligomers), such as AcHN-(RXRRBR)2XB peptide-tagged PMO (R=arginine; X=6-aminohexanoic acid; B=β-alanine), can be cited.

According to a specific embodiment, the antisense oligonucleotides used in the present invention are morpholinos oligos, preferably bound to a group promoting their entry into cells such as an octaguanidine dendrimer, advantageously grafted to one of the extremities of the nucleic acids, and even more advantageously bound covalently to their 3' extremity. Such oligonucleotides are for example sold by the GeneTools Company under the name "Vivo-Morpholinos" and exhibit the following structure:

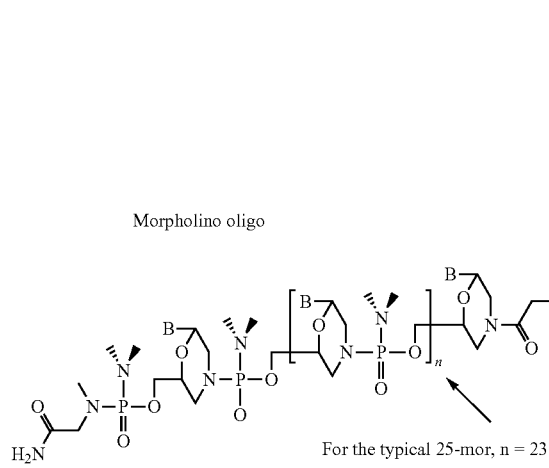
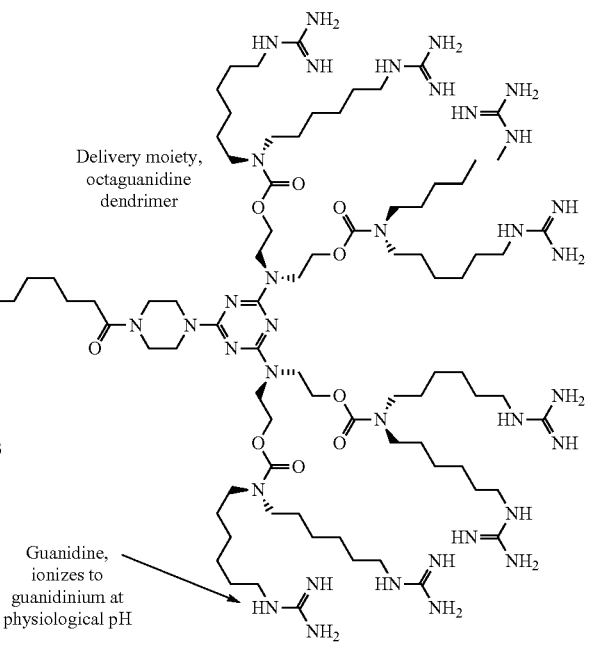

Alternatively, the antisense oligonucleotides of the invention may be administered using a vector. Generally, a vector in the sense of the invention includes but is not restricted to plasmids, phagemides, viruses and other carriers derived from a bacterial or viral source, into which the AON according to the invention have been incorporated.

According to a preferred embodiment, the vector contains sequences obtained from the following viruses: Lentivirus, Retrovirus, Adenovirus, Adeno-associated virus, SV-40 type virus, Herpes virus, and any other appropriate virus known in the art. Of these vectors, Lentiviruses, Retroviruses and Adeno-associated viruses (AAV) are preferred.

According to a particular embodiment, the antisense oligonucleotides are administered in combination with a viral vector, advantageously an AAV vector. According to this aspect, the sequence coding for the antisense oligonucleotide or AON is harboured or carried by the said AAV vector. In other words, the sequence coding for the antisense oligonucleotide or AON is contained within or included within the AAV genome.

Recombinant adeno-associated viral (AAVr) vectors have become powerful gene delivery tools for the treatment of various disorders. AAV vectors possess a number of features that render them ideally suited for gene therapy, including a lack of pathogenicity, moderate immunogenicity, and the ability to transduce post-mitotic cells and tissues in a stable and efficient manner. Expression of a particular gene contained within an AAVr vector can be specifically targeted to one or more types of cells by choosing the appropriate combination of AAV serotype, promoter, and delivery method.

AAVr result from the genetic modification of AAV virus. More than 100 naturally occurring serotypes of AAV are known. Many natural variants in the AAV capsid exist, allowing identification and use of AAVr with properties specifically suited for dystrophic pathologies. AAV viruses may be engineered using conventional molecular biology techniques, making it possible to optimize these particles for cell specific delivery of nucleic acid sequences, for minimizing immunogenicity, for tuning stability and particle lifetime, for efficient degradation, for accurate delivery to the nucleus. As mentioned above, the use of AAV vectors is a common mode of exogenous delivery of DNA as it is relatively non-toxic, provides efficient gene transfer, and can be easily optimized for specific purposes.

Among the serotypes of AAVs isolated from human or non-human primates (NHP) and well characterized, human serotype 2 is the first AAV that was developed as a gene transfer vector. Other currently used AAV serotypes include AAV1, AAV3, AAV4, AAV5, AAV6, AAV7, AAV8, AAV9, AAV10, AAV11 and AAV12.

The AAV viral genome consists of approximately 5000 nucleotides and contains a gene coding for the replication initiator protein (rep), and a gene coding for the structural proteins (cap). The sequences required in cis for the replication of the genome and its packaging are contained in a 130 to 145 nucleotide sequence found at each extremity of the genome (ITR for "inverted terminal repeat").

From these viruses, a large number of recombinant vectors and chimeric AAVr (hybrids) can also be produced and used.

Desirable AAV fragments for assembly into vectors include the cap proteins, including the vp1, vp2, vp3 and hypervariable regions, the rep proteins, including rep 78, rep 68, rep 52, and rep 40, and the sequences encoding these proteins. These fragments may be readily utilized in a variety of vector systems and host cells.

In order to produce the AAVr, such fragments may be used alone, in combination with other AAV serotype sequences or fragments, or in combination with elements from other AAV or non-AAV viral sequences. As used herein, artificial AAV serotypes include, without limitation, AAV with a non-naturally occurring capsid protein. Such an artificial capsid may be generated by any suitable technique, using a selected AAV sequence (e.g., a fragment of a vp1 capsid protein) in combination with heterologous sequences which may be obtained from a different selected AAV serotype, non-contiguous portions of the same AAV serotype, from a non-AAV viral source, or from a non-viral source. An artificial AAV serotype may be, without limitation, a chimeric AAV capsid, a recombinant AAV capsid, or a "humanized" AAV capsid. Thus exemplary AAVs, or artificial AAVs, include AAV2/8 (U.S. Pat. No. 7,282,199), AAV2/5 (available from the National Institutes of Health), AAV2/9 (WO2005/033321), AAV2/6 (U.S. Pat. No. 6,156,303), AAVrh8 (WO2003/042397) and AAVrh10, among others. In one embodiment, the vectors useful in the compositions and methods described herein contain, at a minimum, sequences encoding a selected AAV serotype capsid, e.g., an AAV8 capsid, or a fragment thereof. In another embodiment, useful vectors contain, at a minimum, sequences encoding a selected AAV serotype rep protein, e.g., AAV8 rep protein, or a fragment thereof. Optionally, such vectors may contain both AAV cap and rep proteins. In vectors in which both AAV rep and cap are provided, the AAV rep and AAV cap sequences can both be of one serotype origin, e.g., all of AAV8 origin. Alternatively, vectors may be used in which the rep sequences are from an AAV serotype, which differs from that which is providing the cap sequences. In one embodiment, the rep and cap sequences are expressed from separate sources (e.g., separate vectors, or a host cell and a vector). In another embodiment, these rep sequences are fused in frame to cap sequences of a different AAV serotype to form a chimeric AAV vector, such as AAV2/8 (U.S. Pat. No. 7,282,199).

Recombinant AAV genomes may be prepared from the AAVs in which the genes coding for viral proteins (rep and cap) are deleted, leaving only the two repeated ITR sequences. The production of recombinant vectors requires multiplication and packaging of these recombinant genomes. This stage is usually performed in cultured cells which are transfected with both the recombinant genome of interest and plasmids coding for the missing rep and cap proteins (the cap proteins enable the capsid to be formed). A recombinant genome and rep and cap genes originating from identical or different serotypes can be used. A large number of combinations are therefore possible.

When the serotypes are identical, the only serotype corresponding to the vector is indicated. If the serotypes are different, the so-called hybrid AAVr vectors are obtained for which the serotypes used are indicated. As an example, an AAVr from serotype 2 is understood to have been obtained only from serotype 2. Conversely, a serotype 2/8 AAVr is a vector in which a recombinant genome obtained from a serotype 2 vector has been used whereas the genes coding for the capsid proteins used correspond to the genes from an AAV of serotype 8.

The AAV viral capsid of the AAV virus and as a result of the AAVr vectors have been shown to be generally associated with a specific cellular or tissue tropism.

According to one embodiment, the AAV used in the frame of the invention is advantageously based on an AAV of serotype 2 (AAV2), 5 (AAVS), 8 (AAV8) or 9 (AAV9). According to the invention, the AAV used is advantageously based on a serotype 2 AAV (AAV2), 6 (AAV6), 8 (AAV8), 9 (AAV9) or rh10 (AAVrh10). The capsid is chosen appropriately to enable effective or even preferential transduction of the muscle or nerves. The AAV used may therefore be selected from the following group: AAV2/1, AAV2, AAV2/6, AAV2/8, AAV2/9, AAV2/rh10.

In the AAVr vectors used in the present invention, the AAV genome may be either a single stranded (ss) nucleic acid or a double stranded (ds), or a self complementary (sc) nucleic acid molecule.

Production of the AAVr vectors is well known to the person of the art and can be performed by bi-transfection or tri-transfection of HEK 293 cells, by the herpes simplex viral system or using a baculovirus system. Advantageously, the viral particles are obtained by bi- or tritransfection of HEK 293 cells or using the baculovirus system.

In particular in combination with a viral vector such as a vector derived from a Lentivirus, a Retrovirus or an Adeno-associated virus (AAV), the use of snRNAs ("small nuclear" RNAs), particularly U1, U2, U4, U5, U7, U11 and U12, advantageously U7snARN, may be beneficial.

According to a specific embodiment, the vector according to the invention further contains or comprises a sequence coding for a modified snRNA. More specifically, the sequence coding for the antisense oligonucleotide (AON) according to the invention is introduced or inserted into the sequence coding for the snRNA. In other words, and preferably, the vector of the invention contains a sequence coding for an antisense oligonucleotide, which itself is contained within a sequence coding for a modified snRNA. This embodiment enables an oligonucleotide containing the modified snRNA in which the AON has been incorporated to be expressed. As already stated, incorporation of the AON within a modified snRNA has the effect of stabilising the expression of said oligonucleotide and in addition to enable nuclear expression of these oligonucleotides.

The snRNA ("small nuclear RNA") are small RNA molecules present in a nucleus of cells and involved in certain maturation stages of the pre-messenger RNA. These are called U1, U2, U3 . . . up to U13. It is well-known that native snRNA contains a specific antisense region for the pre-messenger RNA ensuring its maturation. This sequence enables hybridisation to the target pre-messenger RNA. In addition, the region coding for the native snRNA (i.e. the sequence which is actually transcribed) in particular contains a so-called sm domain which codes for an Sm ("small nuclear ribonucleoprotein") protein binding site. This domain is essential for the pre-messenger RNA maturation activity of the snRNA (Grimm et al. EMBO J., 1993, 12(3): 1229-1238). The region coding for the native snRNA also contains a sequence coding for a stem-loop which has been shown to stabilise the binding between the snRNA and the pre-mRNA which is to be matured, thereby facilitating splicing (Sharma et al., Genes Dev., 2014, 28(22): 2518-2531).

In the context of the invention, the terms "sequence coding for a modified snRNA" refer to an oligonucleotide which has the native sequence of the functional snRNA gene in which the sequences involved in the initial function of the snRNA are inactivated and/or modified, advantageously by inserting the sequence coding for the AON according to the invention. As used therein, the terms "native functional gene sequence" refer to the part of the endogenous gene containing the region coding for the snRNA (i.e. the transcribed sequence), together with the 5' and 3' regulatory regions and in particular the native snRNA promoter.

Preferably, the sequence coding for the modified snRNA codes for a type of U7 snRNA. According to this embodiment, the sequence of the Sm protein binding sites is modified in order to inactivate maturation of the pre-messenger RNAs coding for the histones, advantageously by inserting the sequence coding for the AON according to the invention.

As described with regard to this type of snRNA (U7), the sequence of the Sm protein binding sites may also be modified in order to increase the nuclear concentration of snRNA, for example, replaced by an optimised sequence, advantageously the smOPT sequence disclosed by Schümperli and Pillai (Cell. Mol. Life Sci. 60: 2560-2570, 2004).

On the other hand and in order to facilitate the desired splicing, the sequence coding for the stem-loop is preferentially native. In other words, it is advantageously not modified.

As already mentioned, the modified snRNA used in the context of the invention preferably does not contain the native specific antisense sequence hybridising the pre-messenger RNA targeted by this sRNA, in the case of U7snRNA the pre-messenger RNA of the histones. Advantageously, this sequence is replaced by a sequence coding for the antisense oligonucleotide of interest.

In the sense of the invention, the sequence coding for the modified snRNA may also be modified in order to replace the native sequence of the snRNA promoter by the sequence of another promoter, such as the promoter sequence of another snRNA type. By way of example and according to the invention, a "sequence coding for a modified snRNA of the U7 type" designates a sequence coding for a snRNA of the U7 type which has undergone the modifications listed above but which includes the native U7 snRNA promoter. This promoter can be replaced by a promoter from another snRNA such as U1, U2 or U3 type, or by any other appropriate promoter to implement the invention. The different snRNA promotors are well-known and in particular have been described by Hernadez (J Biol Chem.; 2001, 276(29):26733-6).

In the context of the invention, amongst the different types of snRNA, the U7 type (U7snRNA), which is normally involved in maturation of pre-messenger RNA coding for histones, is preferentially used.

In this context, it has also been demonstrated that a specific domain known as the "kiss domain", when fused to the antisense oligonucleotide carried by the snRNA, can hybridise with the stem-loop shaped part of the snRNA. This hybridisation results in a change in the secondary structure of the modified snRNA which improves its binding to the molecular machinery required for splicing. This domain has been described particularly in WO 2011/113889, the content of which should be considered to form part of the present application. It is therefore possible to incorporate a sequence coding for the "kiss domain" as described in this document into the sequence coding for the modified snRNA according to the invention.

In practice, these different modifications can be introduced into sequences coding for the snRNA using usual genetic engineering techniques such as PCR directed mutagenesis.

It should be noted that the snRNA sequences are highly conserved between the different species. The sequence coding for the modified snRNA used in the vector of the invention may therefore be of human or murine origin. Preferentially, the sequence coding for the modified snRNA used in the invention is of murine origin.

The present invention also concerns pharmaceutical compositions containing as an active ingredient at least one antisense oligonucleotide as defined in the present application, as well as the use of this AON or composition as a medicinal product.

According to another aspect, the present invention concerns a composition, advantageously a pharmaceutical composition or a medicinal product containing an AON as described above and potentially other active molecules (other gene therapy proteins, chemical groups, peptides or proteins, etc.) for the treatment of the same disease or a different disease.

The present invention then provides pharmaceutical compositions comprising a nucleic acid of the invention, i.e. an AON according to the invention. Advantageously, such compositions comprise a therapeutically effective amount of said AON, and a pharmaceutically acceptable carrier. In a specific embodiment, the term "pharmaceutically acceptable" means approved by a regulatory agency of the Federal or a state government or listed in the U.S. or European Pharmacopeia or other generally recognized pharmacopeia for use in animals, and humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, sodium stearate, glycerol monostearate, talc, sodium chloride, dried skim milk, glycerol, propylene glycol, water, ethanol and the like.

The composition, if desired, can also contain minor amounts of wetting or emulsifying agents, or pH buffering agents. These compositions can take the form of solutions, suspensions, emulsions, sustained-release formulations and the like. Examples of suitable pharmaceutical carriers are described in "Remington's Pharmaceutical Sciences" by E. W. Martin. Such compositions will contain a therapeutically effective amount of the therapeutic, preferably in purified form, together with a suitable amount of carrier so as to provide the form for proper administration to the subject.

In a preferred embodiment, the composition is formulated in accordance with routine procedures as a pharmaceutical composition adapted for intramuscular or intravenous administration to human beings. Typically, compositions for intravenous administration are solutions in sterile isotonic aqueous buffer. Where necessary, the composition may also include a solubilizing agent and a local anesthetic such as lidocaine to release pain at the site of the injection.

In one embodiment, the composition according to the invention is suitable for administration in humans. The composition is preferably in a liquid form, advantageously a saline composition, more advantageously a phosphate buffered saline (PBS) composition or a Ringer-Lactate solution.

The amount of the therapeutic agent of the invention, i.e. the AON, which will be effective in the treatment of CNM or CMT can be determined by standard clinical techniques. In addition, in vivo and/or in vitro assays may optionally be employed to help predict optimal dosage ranges. The precise dose to be employed in the formulation will also depend on the route of administration, the weight and the seriousness of the disease, and should be decided according to the judgment of the practitioner and each patient's circumstances.

Suitable administration should allow the delivery of a therapeutically effective amount of the therapeutic product to the target tissues, especially skeletal muscles and nerves.

In practice and in relation to the administration of an AON, an appropriate dose is in the range of 1 mg/kg to 100 mg/kg. It is known that as low a dose as possible in order to obtain a satisfactory result is preferred in particular in order to avoid toxicity problems or immune reactions.

Available routes of administration are topical (local), enteral (system-wide effect, but delivered through the gastrointestinal (GI) tract), or parenteral (systemic action, but delivered by routes other than the GI tract). The preferred route of administration of the compositions disclosed herein is parenteral which includes intramuscular administration (i.e. into the muscle) and systemic administration (i.e. into the circulating system). In this context, the term "injection" (or "perfusion" or "infusion") encompasses intravascular, in particular intravenous (IV), and intramuscular (IM) administration. Injections are usually performed using syringes or catheters. According to a specific embodiment and in order to promote a localised therapeutic effect, specific muscular administration methods are preferred, particularly intramuscular injection. Conversely, in order to effectively reach all of the muscles and/or peripheral nerves, systemic administration may be preferred. The so-called loco-regional administration (intravascular under pressure) is also possible.

The frequency of administration may depend on the administration route but also on the form of the AON: when the use of a naked AON involves periodic and repeated injections, a single injection of a vector-carried AON may be sufficient.

Several administrations under different conditions may be considered, particularly:
Repeated administration of the same AON by the same administration route;
Administration of the same AON to different sites particularly to different limbs;
Administration of different AON by the same administration route;
Administration of different AON by different administration routes.

As already stated, the patient is advantageously a human, particularly a new born, a young child, a child, an adolescent or an adult. The therapeutic tool according to the invention, however, may be adapted and useful for the treatment of other animals, particularly pigs, mice, dogs or macaque monkeys.

Such medicinal products are particularly intended for the treatment of centronuclear myopathies (CNM) and Charcot-Marie-Tooth disease (CMT). Advantageously, in the context of the invention, patients targeted are those with increased levels of dynamin 2 (due to increased gene expression or protein activity) and/or having a mutated dynamin 2.

A treatment according to the invention therefore uses theoretically effective quantities of AON with the aim of reducing the symptoms of such diseases, particularly atrophy, hypotonia and muscle weakness in the case of CNM. More specifically, a treatment according to the invention is intended to reduce or delay the development of symptoms and phenotypes of said diseases. In relation to centronuclear myopathies, this means to improve motor muscle behaviour and increase life expectancy particularly by restoring at least to some extent the intracellular organisation of the myofibres, including the position of the nuclei and the organisation of triads and T tubules.

According to one aspect, the treatment with an AON according to the invention is combined with administration of another treatment, advantageously dedicated to the treatment of the same disease.

According to a specific embodiment, the centronuclear myopathy is myotubular myopathy (XLMTM). In this context, treatment with an AON according to the invention may be combined with administration of myotubularin (MTM1), for example using the recombinant vector described in document US2015/258215.

According to another aspect, the treatment according to the invention is dedicated to patients having Charcot-Marie-Tooth disease (CMT), particularly those carrying mutations in the DNM2 gene or in other genes resulting in increased levels of dynamin 2, especially in nerves. According to a specific embodiment, the treatment is for the dominant intermediate CMT (DI-CMTB), the axonal CMT (CMT2M), CMTDIB, CMTDI1, or the CMT type 4B (CMT4B including CMT4B1/CMT4B2). In that context, treatment with an AON may be combined with administration of a "corrected" (native) version of the mutated protein(s), e.g. MTMR2 or the highly homologous MTM1 for the treatment of CMT4B1, and MTMR13 for the treatment of CMT4B2.

In view of the remarkable effects reported in the present application, the invention also concerns the use of an AON as described above or of a composition containing this AON for the manufacture of a medicinal product, advantageously intended for the prevention or treatment of centronuclear myopathies (CNM), particularly myotubular myopathy (XLMTM), and Charcot-Marie-Tooth disease (CMT) as defined above.

In other words, the present invention provides a method for the therapeutic or prophylactic treatment of the centronuclear myopathies (CNM) and Charcot-Marie-Tooth disease (CMT) as defined above, involving administration of such an AON or a composition containing this AON to a subject or patient.

According to another aspect, the present invention concerns a kit or pack containing an AON according to the invention, possibly in vector-carried form or formulated in a pharmaceutical composition. This is advantageously present in a suitable container such as a syringe. In addition, the kit advantageously contains instructions for use of the said AON particularly relating to it storage, preparation for injection and/or administration. This kit may contain an appropriate solution for its dissolution or dilution.

Examples

The invention and its advantages are understood better from the examples shown below supporting the annexed figures. In particular the present invention is illustrated with regard to antisense oligonucleotides (AON) in the form of morpholino bound to an octa-guanidine dendrimer (PMO) tested in a murine model (Mtm1-KO) which mimics the symptoms of myotubular myopathy. These examples are not however in any way limiting.

(A) Representative images of western blots obtained with dynamin 2 (98 kDa) after treatment with PMO A, B, C, D, E, or F in C2C12 cells and (B) their quantification after normalisation with GAPDH. n=4, 2 independent experiments.

Figure 2:
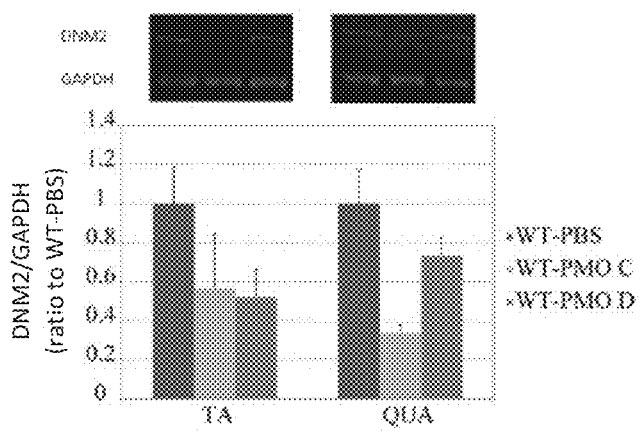
Figure 2:
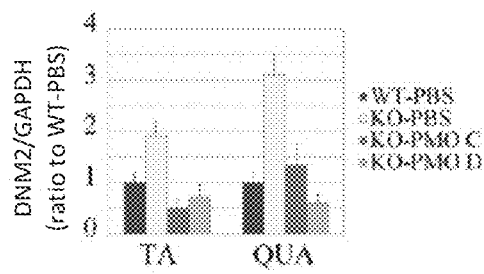

FIG. 2: Level of dynamin 2 protein expression after treatment of TA (Tibialis Anterior) and QUA (Quadriceps) muscles in normal (A) or Mtm1-KO (B) mice with PMO.

(A) Representative images of Western blots obtained with dynamin 2 (98 kDa) and the muscles of WT mice treated with PBS (n=4) or PMO C and D (n=2 for each condition), and their quantification after normalisation with GAPDH.

(B) Quantification after normalisation with GAPDH of dynamin 2 levels in KO mice treated with PBS (n=10 for the TA and n=11 for the QUA) or with PMO C (n=6) and D (n=4 for the TA and n=5 for the QUA).

Figure 3:
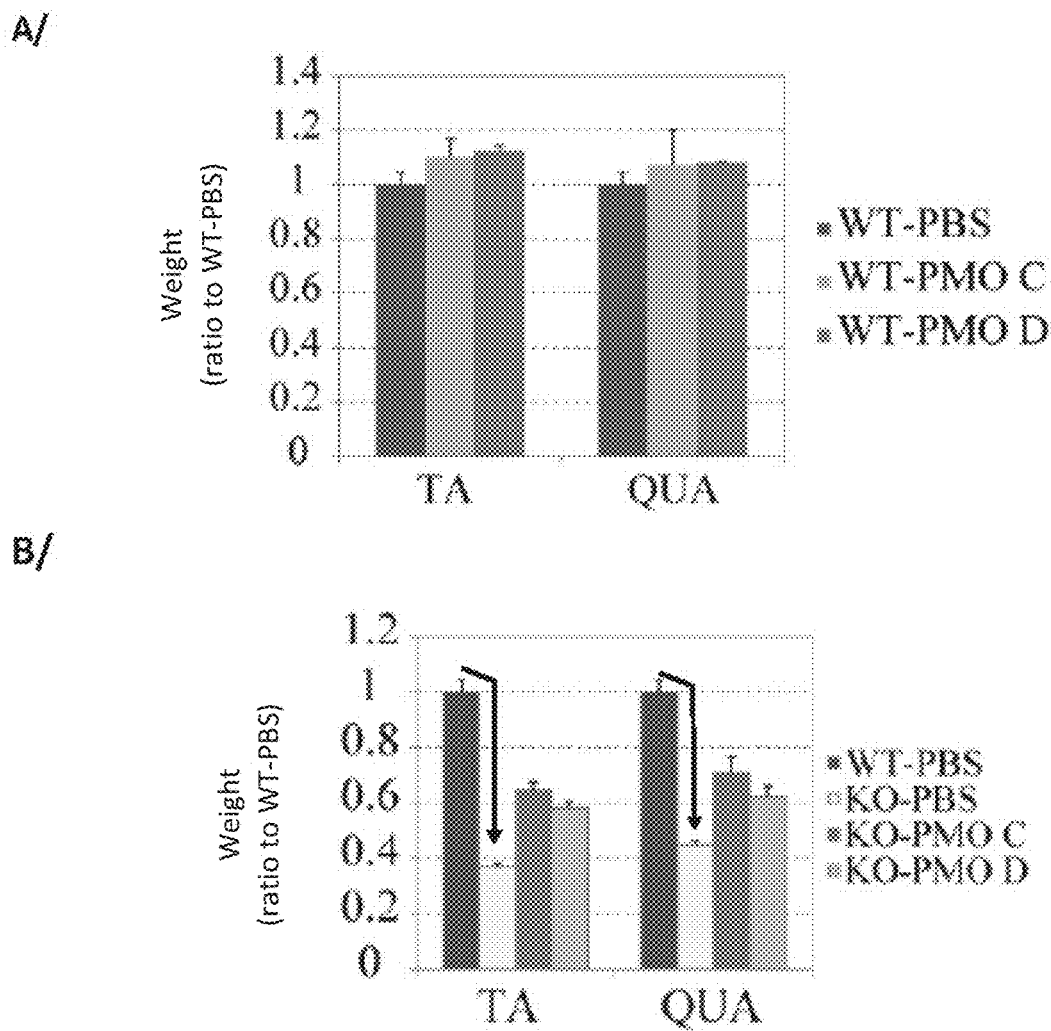

FIG. 3: Measurement of muscle weight after treatment with the PMO.

Histograms showing muscle weight of TA and QUA muscles (A) in normal (WT) mice treated with PBS (n=6) or with PMO C and D (n=2 for each condition)

(B) in Mtm1-KO mice treated with PBS (n=20) or with PMO C (n=6) and D (n=5).

Figure 4A:
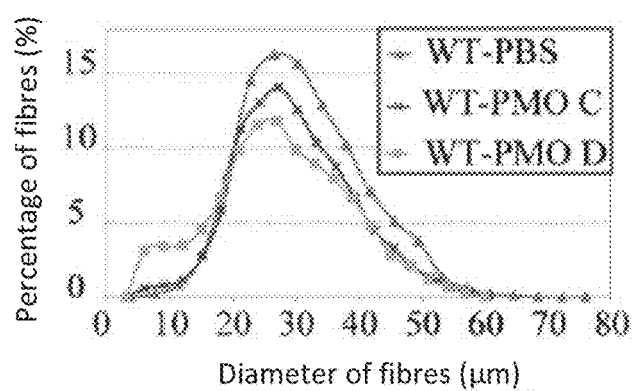
Figure 4B:
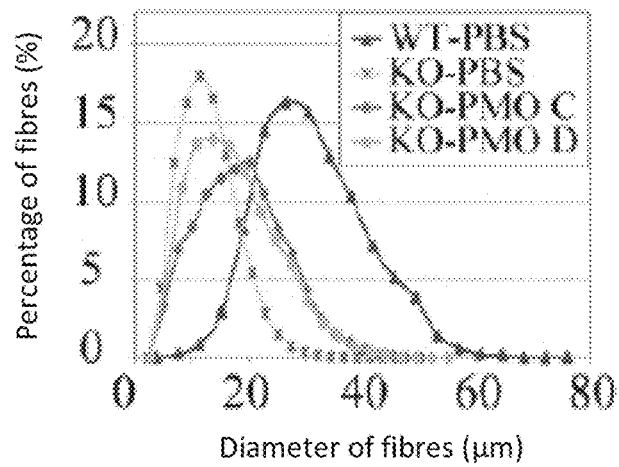

FIG. 4: Distribution of muscle fibre diameter after treatment of the TA with the PMO.

Graphs showing the percentage of fibres by diameter in the TA (A) in normal (WT) mice treated with PBS (n=4) or with PMO C and D (n=2 for each condition)

(B) in Mtm1-KO mice treated with PBS (n=10) or with PMO C (n=6) and D (n=4).

Figure 5:
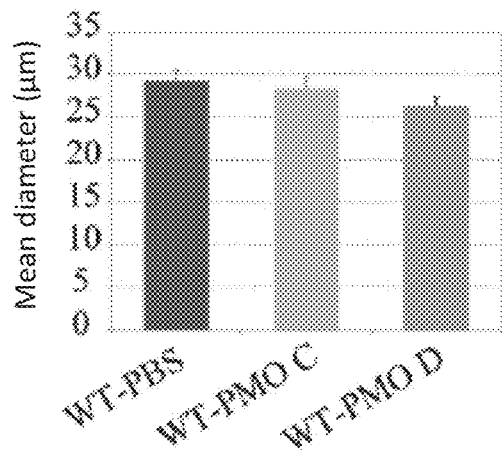
Figure 5:
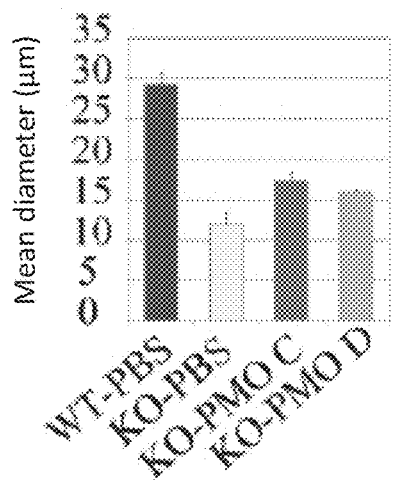

FIG. 5: Measurement of muscle fibre diameter after treatment of the TA with the PMO.

Histograms showing mean fibre diameter under the conditions of FIG. 4.

Figure 6:
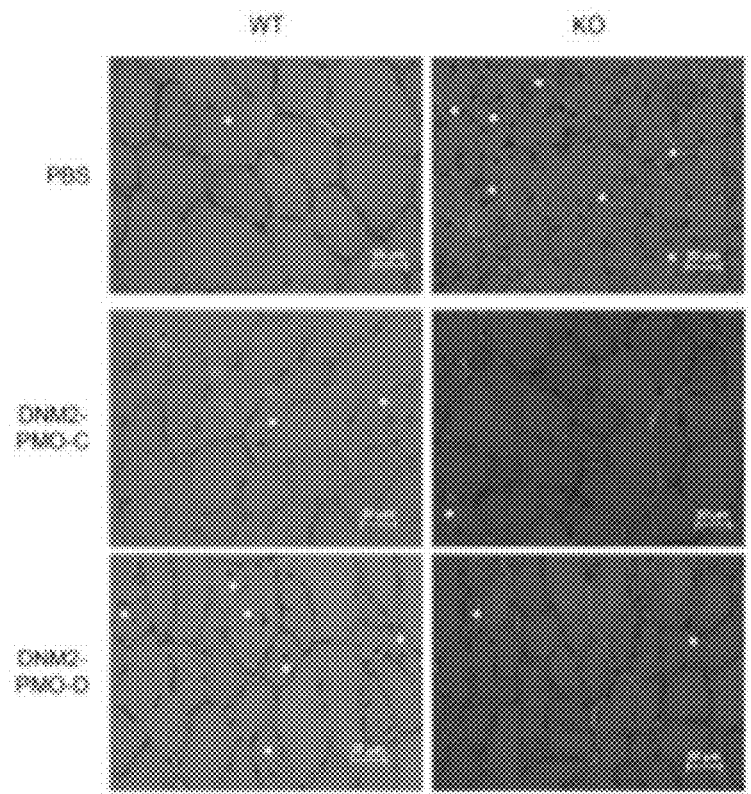

FIG. 6: HE staining of the TA after treatment with the PMO.

Representative images of HE staining performed on transverse TA sections in normal mice (WT on the left) and Mtm1-KO mice (KO on the right) treated with PBS or with PMO C or PMO D. *: internalised nuclei.

Figure 7:
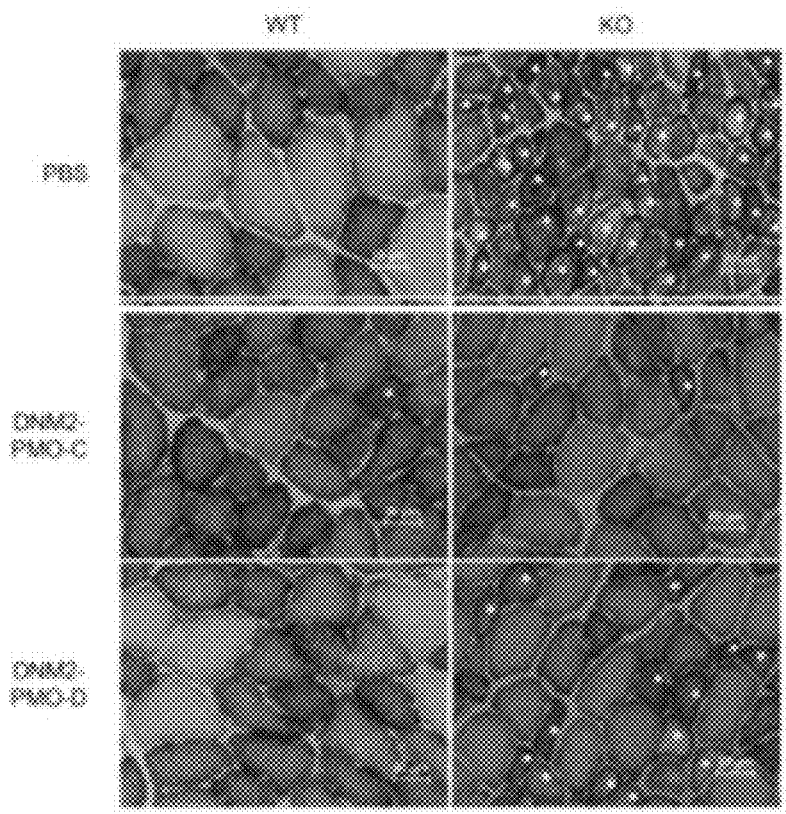

FIG. 7: NADH staining of the TA after treatment with the PMO.

Representative images of NADH staining performed on transverse TA sections in normal mice (WT on the left) and Mtm1-KO mice (KO on the right) treated with PBS or with PMO C or PMO D.*: "necklace" (subsarcolemmal accumulation of mitochondria).

Figure 8:
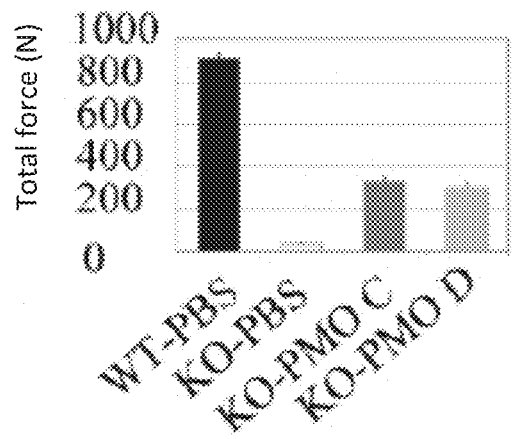

FIG. 8: Measurement of total muscle force in the TA in situ after treatment of muscles with the PMO.

Graphs showing total TA force in normal mice treated with PBS (n=6) and the TA of Mtm1-KO mice treated with PBS (n=18) or with PMO C (n=6) or D (n=4).

Figure 9:
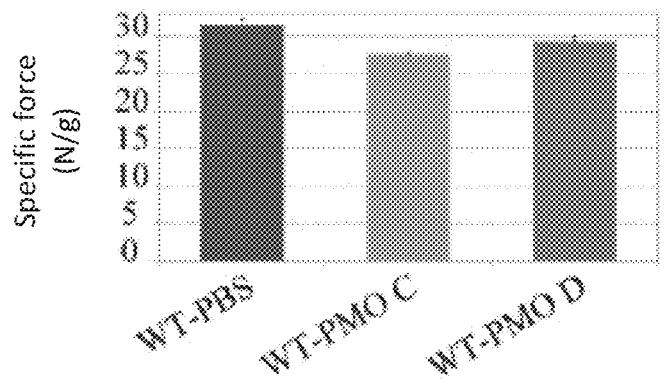
Figure 9:
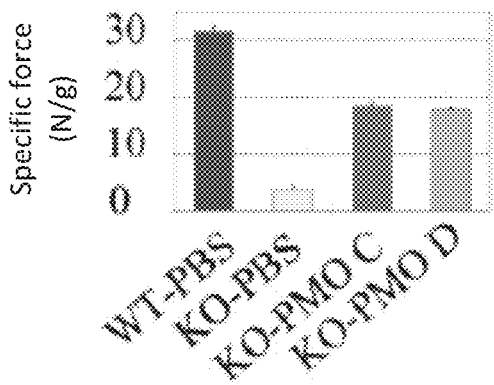

FIG. 9: Measurement of specific TA force in situ after treatment of muscles with the PMO.

Graphs showing the specific force of TA treated under the following conditions:

(A) normal (WT) mice treated with PBS (n=6) or with PMO C (n=2) or D (n=2)

(B) Mtm1-KO mice treated with PBS (n=18) or with PMO C (n=6) or D (n=4).

Specific force is calculated as the ratio of total force to muscle weight.

Figure 10:
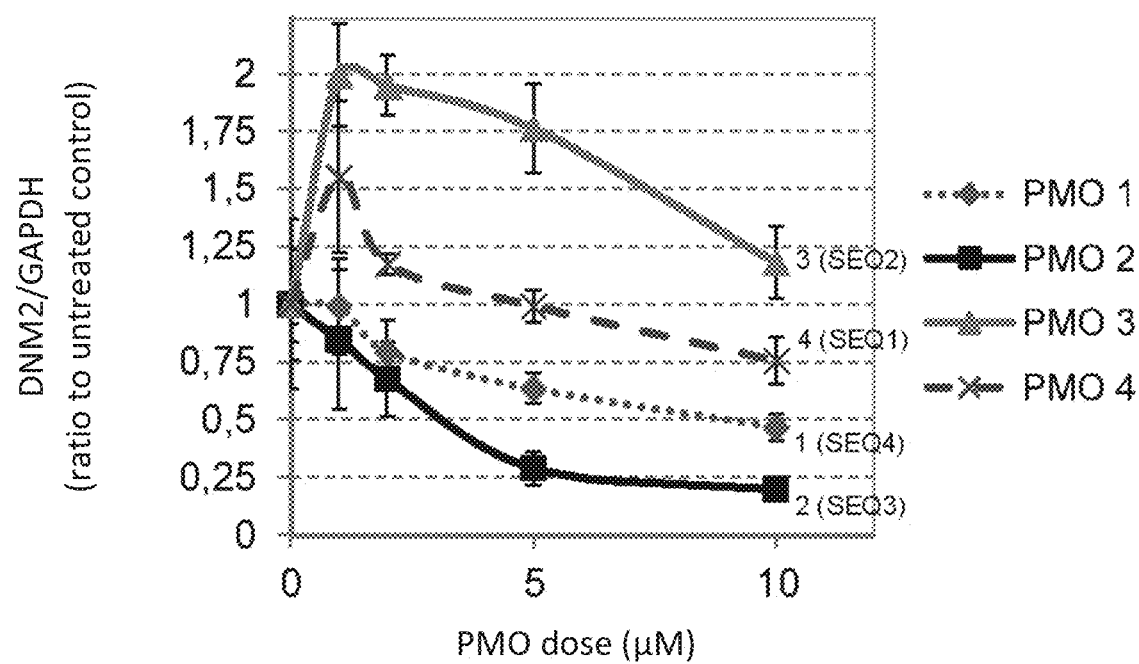

FIG. 10: Level of dynamin 2 protein expression after treatment of human cells with the PMO.

Quantification, after GAPDH normalisation, of dynamin 2 levels after treatment with human antisense PMO 1, 2, 3, or 4 in KM155C25 cells.

A. MATERIALS AND METHODS

1/Morpholinos

Six antisense morpholinos oligonucleotides targeting different murine Dnm2 pre-mRNA regions (NM_001253893.1) and four morpholinos antisense oligonucleotides targeting different human Dnm2 pre-mRNA regions (NM_001005360.2) were synthesised and conjugated to an octa-guanidine dendrimer promoting penetration into the cell (Vivo-Morpholino, Gene Tools, LLC) (Table 1).

TABLE 1

Sequence of Vivo-Morpholinos oligonucleotides and target regions on the murine and human dynamin 2 pre-mRNA. * Position of the region with regard to the ATG.

| Name of Vivo-Morpholino | AON sequence | Target sequence | Target region |
|---|---|---|---|
| PMO A | CGACTAAGACTCTCGGTTCCGATGT (SEQ ID NO: 5) | ACATCGGAACCGAGAGTCTTAGTCG (SEQ ID NO: 11) | 5' UTR * -28/-53 |
| PMO B | TCATCCGGTTCTCAGGCGACACC (SEQ ID NO: 6) | GGTGTCGCCTGAGAACCGGATGA (SEQ ID NO: 12) | 5' UTR * -152/-174 |
| PMO C | CCCTGAATTTCTATTTCTCATACCT (SEQ ID NO: 7) | AGGTATGAGAAATAGAAATTCAGG (SEQ ID NO: 13) | exon 2-intron 2 |
| PMO D | GGTGGCCTCAAACCTCCGCTATACC (SEQ ID NO: 8) | GGTATAGCGGAGGTTTGAGGCCAC (SEQ ID NO: 14) | exon 6-intron 6 |
| PMO E | TTGCCCATGGTGTCCGCCTC (SEQ ID NO: 9) | GAGGCGGACACC(ATG)GGCAA (SEQ ID NO: 15) | ATG |
| PMO F | TTGCTTCCTCCTGCTCTGCTC (SEQ ID NO: 10) | GAGCAGAGCAGGAGGAAGCAA (SEQ ID NO: 16) | 5' UTR * -65/-90 |
| PMO 1 | GACCCTAACGACCTGGCCCC (SEQ ID NO: 4) | GGGGCCAGGTCGTTGAGGGTC (SEQ ID NO: 17) | 5' UTR * -49/-70 |
| PMO 2 | TCGGCCGCCCATTTTACCTGTTTA (SEQ ID NO: 3) | AAACAGGTAAAATGGGGCGGCCTG (SEQ ID NO: 18) | exon 2-intron 2 |
| PMO 3 | CGTGCAAACCCTTGCAGTACCTGAT (SEQ ID NO: 2) | ATCAGGTACTGCAAGGGTTTGCAC (SEQ ID NO: 19) | exon 6-intron 6 |
| PMO 4 | CTGGACCATCCTATGAGGAAAAGGA (SEQ ID NO: 1) | TCCTTTTCCTCATAGGATGGTCCAG (SEQ ID NO: 20) | exon 8-intron 7 |

2/Ex Vivo Screening

Screening of Murine Vivo-Morpholinos:

Murine C2C12 myoblasts are incubated for 48 hours at 37° C. in a DMEM medium (Thermo Fisher scientific) supplemented with foetal calf serum (FCS; Thermo Fisher scientific) at a concentration of 10%, containing 0, 1, 2 and 5 µM of each Vivo-Morpholino. The cells are collected by centrifugation at 4° C. (5 min; 800 rpm), washed in PBS (Phosphate Buffer Saline, Gibco®) and the cell pellets are then recovered by centrifugation at 4° C. (10 min; 12 000 rpm).

Screening of Human Vivo-Morpholinos:

KM155C25 myoblasts are incubated for 48 hours at 37° C. in a "Skeletal Muscle Cell Growth Medium" (Promo Cell) supplemented with foetal calf serum (FCS; Thermo Fisher scientific) at a concentration of 15%, containing 0, 1, 2 and 5 µM of each Vivo-Morpholino. The cells are collected by centrifugation at 4° C. (5 min; 800 rpm), washed in PBS (Phosphate Buffer Saline, Gibco®), collected by 2 successive centrifugations (5 min at 80 g) and the cell pellets are then recovered by centrifugation at 4° C. (10 min; 12000 rpm).

3/Murine Lines and Treatments

KO ("Knock-out") mice inactivated for the MTM1 gene (Mtm1-KO model), genetic background BS53d4-Pas, exhibit complete absence of myotubularin in all of their body tissues and have profound abnormalities of skeletal muscle mass, structure and function. The murine phenotype is similar to the phenotype seen in XLMTM human patients although unlike human beings in which the disease is congenital, it is progressive and only develops at around 3 weeks old. The mice survive on average for less than 2 months.

The morpholinos are diluted to a concentration of 0.5 µg/µL in PBS and administered intramuscularly into the muscles of normal mice (WT: "Wild-type") or Mtm1-KO (KO) mice aged 3 weeks old, at a dose of 10 µL (5 µg) into the left TA (Tibialis Anterior) muscles and 40 µL (20 µg) into the left QUA (Quadriceps) muscles. The contralateral right muscles received equivalent respective volumes of PBS.

The mice are killed at the age of 5 weeks old, after assessment of their muscle function and samples of the TA and QUA muscles are taken. After being sampled, the whole muscles are weighed and then cut into two transversely. The proximal part of the muscle is weighed and frozen in liquid nitrogen whereas the distal part is frozen horizontally in cold isopentane. All of the muscles sampled are stored at −80° C.

4/Molecular Analyses

Western-Blot

The proteins are extracted in lysis buffer containing 10 mM Tris HCl pH 7.4, 150 mM NaCl, 5 mM EGTA, 2 mM sodium orthovanadate, 100 mM sodium fluoride (NaF), 4 mM sodium pyrophosphate, "Protease Inhibitor Cocktail" (Roche Applied Sciences), 1% Triton X-100 and 0.5% IGEPAL (Sigma-Aldrich). The muscle samples are also homogenised by grinding mechanically using the Fast-Prep® system (MP Biomedicals) and are then incubated on ice shaking occasionally for 30 (KM155C25 proteins) and 45 (C2C12 proteins and muscles) minutes, respectively. After centrifugation at 4° C. (10 min; 12,000 g), the supernatants are recovered for Western-Blot analysis. Protein concentrations are measured using the Bradford method (Bio-Rad). Total proteins are denatured for 10 min at 100° C. in a "Sample Buffer 4X" buffer (Bio-Rad) supplemented with 80 mM DTT (Dithiothreitol, Sigma-Aldrich), separated in NuPAGE® Bis-Tris gradient gels (Thermo Fisher Scientific) and then transferred onto PVDF membranes (GE Healthcare). The membranes are blocked overnight at 4° C. in a blocking buffer "Odyssey Blocking Buffer" (LI-COR) and are then incubated in the presence of a rabbit anti-dynamin 2 polyclonal antibody (Abcam) and a mouse anti-GAPDH monoclonal antibody (EMD Millipore). Detection is carried out using a secondary rabbit anti-IgG antibody bound to IRDye 800 nm (LI-COR) for dynamin 2 and a mouse secondary anti-IgG antibody bound to Alexa Fluor 680 nm (Life Technologies) for GAPDH. Signals are detected and quantified using the Odyssey infrared imaging system (LICOR).

5/Histological Analyses

HE (Hematoxylin-Eosin) Staining

Haematoxylin is a basic dye which has affinity for negatively charged cell components, particularly nucleic acids and therefore stain the nuclei blue. Eosin is an acid dye which has affinity for positively charged cell parts and the cytoplasm therefore is stained red. Transverse sections of muscles 8 µm thick are stained with haematoxylin-eosin (HE) using standard procedures (Autosteiner, Leica).

NADH (Nicotinamide Adenine Dinucleotide) Staining

NADH staining visualises the location of mitochondria and the endoplasmic reticulum. The sections are incubated for 10 min at 37° C. in 50 mM Tris buffer pH 7.2-7.4, 1.2 mM Nitroblue Tetrazolium (Sigma-Aldrich) and 0.6 mM DPNH (β-Nicotinamide Adenine Dinucleotide, reduced disodium salt hydrate, Sigma-Aldrich), washed in cold distilled water, dehydrated in the same way as for HE staining and Eukitt-mounted.

Laminin Immunolabeling

Laminin is a muscle cell basal membrane protein which delineates the fibre diameter. After blocking, the muscle sections are placed in contact with primary rabbit anti-laminin antibody (polyclonal, dilution 1/1000 in PBS, Dako) and rinsed 3 times in PBS before being incubated with the secondary antibody (Kit EnVision™ HRP Rabbit, Dako). The slides are rinsed again in PBS and then placed in contact for 2 to 5 min with DAB (Diaminobenzidine, Dako) and rinsed with tap water. They are passed successively through baths of 70%, 95% and 100% ethanol and then xylene, and subsequently bounded on Eukitt (Labonord).

The HE, NADH and laminin slides are scanned at 10× magnification on an Axio Scan.Z1 (Zeiss) using the Genethon imaging platform. A plugin combined with ImageJ software developed by Genethon (Histoquant Version 4) is used to determine the number and diameter of fibres on the laminin labellings.

6/Analysis of Muscle Function

This analysis is performed by in situ measurement of TA force in the mouse. It involves testing optimal stretching and optimal tetanus frequency (repeated electrical stimulations leading to summation and fusion of muscle twitching) at which the muscle develops its maximum force during a muscle contraction which does not require any movement.

The distal TA tendon is isolated and connected to a force transducer whereas the sciatic nerve which has previously been isolated is attached to an electrode. An initial tetanus is performed at 70 Hertz-300 ms and the muscle is stretched until it reaches its maximum force. Maintaining this length (L0), the muscle is then subjected to increasing tetanus actions from 80 to 125 Hertz until its maximum force is obtained. The maximum muscle force (P0) is measured at its optimal stretching and frequency. The specific maximum force (sP0) is calculated as the ratio of the total force developed by the muscle to its weight.

7/Statistical Analyses

Results have been expressed as mean±SEM ("Standard Error of the Mean"). Data were analysed for normal distributions using the Kolmogorov-Smirnoff test and individual mean values were compared using the non-parametric Mann-Whitney test. Differences were deemed to be statistically significant for $P<0.05$, $P<0.01$ and $P<0.001$.

B. RESULTS

B-I/Study of the Murine PMO:

In order to assess the therapeutic potential of the PMO targeting the Dnm2 gene, the reduction in dynamin 2 expression was measured in vitro and the best PMO were then tested in vivo on normal mice or mice suffering from myotubular myopathy (Mtm1 KO).

Figure 1:
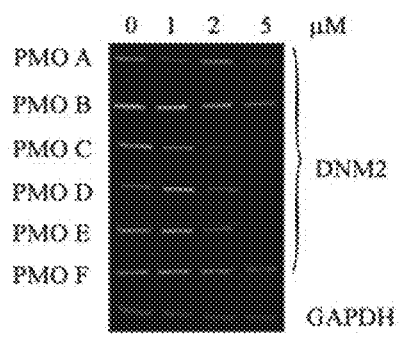
FIG. 1: Level of dynamin 2 protein expression after treatment of murine cells with PMO.
Figure 1:
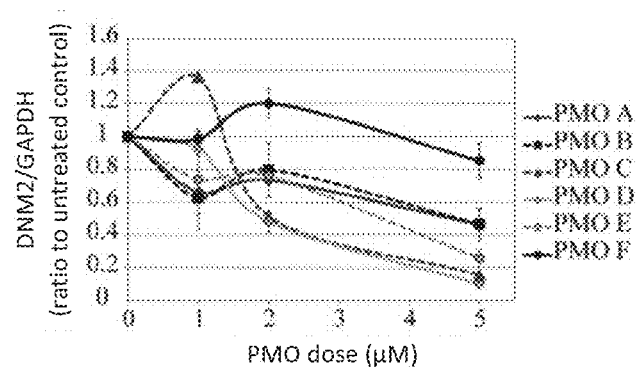

1/Inhibition of Dynamin 2 Expression by the PMO in C2C12 Myoblasts:

In an initial stage, the effectiveness of the PMO targeting the Dnm2 gene was assessed in vitro on C2C12 cells exposed for 48 h to increasing concentrations of the six PMO targeting the Dnm2 gene (0, 1, 2 and 5 µM), respectively. From the cell protein extracts the levels of dynamin 2 expression were quantified using Western-blot (FIG. 1).

Only PMO F appeared to be relatively ineffective in C2C12 cells. Although their effect was variable, expression of dynamin 2 was inhibited by the 5 other PMO: PMO A and B performed least, PMO-E had an intermediary effect whereas PMO C and PMO D which interfere with Dnm2 splicing were the most effective with approximately 50% inhibition at a concentration of 2 µM (with 90% inhibition of dynamin 2 expression at 5 µM).

At the end of the in vitro test, the most effective PMO (PMO C and D) were selected to inhibit expression of dynamin 2 in vivo. The PMO were tested in two types of muscles: in a first stage, in normal mice (WT) muscles in order to establish the effective dose of PMO without toxic effects and once the dose had been defined, in muscles of Mtm1-KO mice in order to measure the therapeutic effects.

2/In Vivo Reduction of Dynamin 2 Expression by the PMO:

The two PMO targeting the Dnm2 gene were injected into the left TA (5 µg) or QUA (20 µg) 3 week old normal (WT) mice and then 3 week old Mtm1-KO mice whereas the contralateral muscles received equivalent doses of PBS. After treatment for two weeks, dynamin 2 expression was quantified in these muscles using Western-blot (FIG. 2).

TA and QUA of the normal mice were treated with PMO C and D to precisely define the dose to be used to avoid reducing the level of dynamin 2 excessively, as absence of dynamin 2 can be lethal in mice. At the doses tested both PMO reduced dynamin 2 expression below normal levels, reaching a minimum of 34% of the normal level in the QUA treated with PMO C.

As expected, expression of dynamin 2 was greatly increased in the muscles of Mtm1-KO mice (approximately 2 and 3 times the normal level in the TA and QUA, respectively). As in the in vitro study, PMO C and D reduced dynamin 2 expression in the TA and QUA in these mice. PMO C was more effective than PMO D in the KO TA (49% of the dynamin 2 level in the TA of normal mice treated with PBS for PMO C compared to 72% for PMO D), whereas PMO D appeared to be more effective in the QUA (61% of the dynamin 2 level in the QUA of normal mice treated with PBS).

3/EFFECT of the PMO on Mouse Phenotype:

3-1 Analysis of the Physical Characteristics of Muscles:

In order to determine the effect on muscle hypotrophy, the weight of the TA and QUA muscles (FIG. 3) and the diameter of the TA fibres (FIGS. 4 and 5) in both normal (WT) and Mtm1-KO mice PMO treated and PMO untreated were measured.

The weight of the Mtm1-KO muscles (TA and QUA) treated with PBS was significantly less than the weight of the normal muscles (approximately 60% weight loss in the TA and 50% in the QUA), confirming the tissue hypotrophy. When the muscles were treated with PMO C and D, a large significant increase in weight is found both in the TA and in the QUA (average 50% increase in weight in the TA and 30% in the QUA). PMO C was slightly more effective than PMO D in both muscles (FIG. 3B).

In order to establish whether the increase in muscle mass is due to an increase in fibre size, fibre diameter was measured after delineating the fibres by labelling with laminin, the major protein in the basal layer (FIG. 4).

When the Mtm1-KO TA were treated with PMO C or D, the fibre diameter curves were shifted towards larger sized fibres (FIG. 4B) and a significant increase in mean fibre diameter was found compared to the mean diameter of KO TA treated with PBS (45% increase for PMO C and 34% for PMO D; FIG. 5B). On the other hand, the mean number of fibres remained the same (results not shown). The increase in muscle weight therefore correlated with an increase in mean fibre diameter and not with an increase in the number of fibres, reflecting a substantial reduction in the TA muscle hypotrophy in Mtm1-KO mice which was particularly high for PMO C.

3-2 Analysis of the Histological Characteristics of Muscles:

The effect of treatments with the different PMO was then studied by muscle histology. To do this, the HE stains which reveal the general histology (fibre shape, position of the nuclei) were produced on transverse TA sections (FIG. 6). NADH stains which locate the mitochondria and sarcoplasmic reticulum (FIG. 7) were also prepared.

The HE staining in the TA of Mtm1-KO mice treated with PBS showed hypotrophic skeletal muscle fibres which were variable in size with numerous internalised or centrally positioned nuclei.

After treatment with the PMO, as seen above from measurement of fibre diameter, the muscle hypotrophy in the TA of Mtm1-KO mice was reduced. Moreover, the fibre size and the general muscle structure appeared more homogeneous (FIG. 6).

However, for all of the PMO tested, no reduction was found in the number of centrally positioned nuclei under the conditions tested (results not shown).

NADH labelling accumulated beneath the circumference of the fibres in the TA of Mtm1-KO mice treated with PBS, in the sub-sarcolemmal position forming "necklaces" which are characteristic of the disease. Labelling in the majority of fibres was distributed more homogeneously and less under the sarcolemma in the TA of Mtm1-KO mice treated with the PMO, reflecting relocation of the organelles (FIG. 7).

3-3 Analysis of the Functional Characteristics of Muscles

In order to confirm that restoration of the main molecular and histological characteristics also restored muscle function, muscle force of the TA was measured in situ (FIGS. 8 and 9).

A significant reduction in muscle force was found in the TA of Mtm1-KO mice (FIG. 9B) compared to the normal animals (WT) which received a PBS injection (95% loss in total force and 87% loss in specific force).

With PMO C and D, the total and specific forces increased very considerably although the specific force increased less than total force (gain of approximately 600% and 250% for total and specific forces, respectively). In the same way as for the improvement in muscle hypotonia, PMO C was slightly more effective than PMO D.

B-II/Study of Human PMO:

In view of the efficacy found in mice, particularly for PMO C and PMO D, the sequences corresponding to sequences SEQ ID NO: 7 and SEQ ID NO: 8 and targeting the same regions on the human gene were obtained. The corresponding antisense (AON) intended for administration to humans were the following sequences:

AON targeting the junction between exon 2 and intron 2 (PMO 2):

TCAGGCCGCCCCATTTTACCTGTTT; (SEQ ID NO: 3)

AON targeting the junction between exon 6 and intron 6 (PMO 3):

CGTGCAAACCCTTGCAGTACCTGAT. (SEQ ID NO: 2)

Furthermore, two additional human AON were tested on human myoblasts:

AON targeting the 5'UTR region (PMO 1):

GACCCTCAACGACCTGGCCCC; (SEQ ID NO: 4)

AON targeting the junction between intron 7 and exon 8 (PMO 4):

CTGGACCATCCTATGAGGAAAAGGA. (SEQ ID NO: 1)

The results are shown in FIG. 10. The AON tested were effective resulting in a fall in the level of expression of human dynamin 2. Under the experimental conditions on this cell type, these Vivo-Morpholinos can be classified in the following order of efficacy: PMO 2>PMO 1>PMO 4>PMO 3.

CONCLUSIONS

The PMO C and PMO D antisense agents selected after in vitro screening reduce levels of expression of dynamin 2 both in vitro and in vivo. The level of dynamin 2 should be regulated precisely as although a 50% reduction in DNM2$^{+/-}$ animals has no phenotypic consequences, complete absence of the protein (DNM2$^{-/-}$ mice) is lethal. At the end of the study, dynamin 2 levels were below normal levels in Mtm1-KO mouse muscles although expression was close to 50% of the normal level indicating that the dose and frequency of administration are appropriate.

The treatment can produce a large increase in total and specific force. In addition, the weight and average size of the muscle fibres increased indicating a reduction in muscle hypotrophy. Moreover, the changes in the distribution of mitochondria and proteins associated with the triads, characteristic of the muscular phenotype of the disease were partially corrected after treatment.

In conclusion, it has been shown in this study that the vivo-morpholinos tested, particularly PMO C and PMO D, are molecules with great therapeutic potential for myotubular myopathy at the doses used for effective in vivo injections, offering promising future treatment prospects in humans.

In addition the human versions of the vivo-morpholinos tested confirmed that the genomic regions targeted were relevant in terms of reducing expression of human dynamin 2.

REFERENCES

Bitoun, M. et al. Mutations in dynamin 2 cause dominant centronuclear myopathy. *Nat Genet* 37, 1207-1209, doi: 10.1038/ng1657 (2005).

Bolino A. et al. Charcot-Marie-Tooth type 4B is caused by mutations in the gene encoding myotubularin-related protein-2. *Nat Genet.* 25(1):17-9 (2000).

Chen S. et al. Phenotype variability and histopathological findings in patients with a novel DNM2 mutation. *Neuropathology* 38(1):34-40 (2018).

Cowling, B. S. et al. Increased expression of wild-type or a centronuclear myopathy mutant of dynamin 2 in skeletal muscle of adult mice leads to structural defects and muscle weakness. *Am J Pathol* 178, 2224-2235, doi: 10.1016/j.ajpath.2011.01.054 (2011).

Cowling, B. S. et al. Reducing dynamin 2 expression rescues X-linked centronuclearmyopathy. *J Clin Invest* 124, 1350-1363, doi:10.11723C171206 (2014).

Ferguson, S. M. & De Camilli, P. Dynamin, a membrane-remodelling GTPase. *Nat Rev Mol Cell Riot* 13, 75-88, doi:10.1038/nrm3266 (2012).

Jones, S. M., Howell, K. E., Henley, J. R., Cao, H. & McNiven, M. A. Role of dynamin in the formation of transport vesicles from the trans-Golgi network. *Science* 279, 573-577 (1998).

Jungbluth, H., Wallgren-Pettersson, C. & Laporte, J. Centronuclear (myotubular) myopathy. *Orphanet J Rare Dis* 3, 26, doi:10.1186/1750-1172-3-26 (2008).

Kojima, C. et al. Regulation of Bin1 SH3 domain binding by phosphoinositides. *EMBO J* 23, 4413-4422, doi:10.1038/sj.emboj.7600442 (2004).

Laporte J. et al. A gene mutated in X-linked myotubular myopathy defines a new putative tyrosine phosphatase family conserved in yeast. *Nat Genet.* 13(2):175-82 (1996).

Marks, B. et al. GTPase activity of dynamin and resulting conformation change are essential for endocytosis. *Nature* 410, 231-235, doi:10.1038/35065645 (2001).

Nicot, A. S. et al. Mutations in amphiphysin 2 (BIN1) disrupt interaction with dynamin 2 and cause autosomal recessive centronuclear myopathy. *Nat Genet.* 39(9): 1134-9 (2007).

Pareyson D et al. New developments in Charcot-Marie-Tooth neuropathy and related diseases. *Curr Opin Neurol.* 30(5):471-480 (2017).

Romero, N. B. Centronuclear myopathies: a widening concept. *Neuromuscul Disord* 20, 223-228, doi:10.1016/j.nmd.2010.01.014 (2010).

Royer, B. et al. The myotubularin-amphiphysin 2 complex in membrane tubulation and centronuclear myopathies. *EMBO Rep* 14, 907-915, doi:10.1038/embor.2013.119 (2013).

Schmid, S. L. & Frolov, V. A. Dynamin: functional design of a membrane fission catalyst. *Annu Rev Cell Dev Biol* 27, 79-105, doi:10.1146/annurev-cellbio-100109-104016 (2011).

Züchner S, et al. Mutations in the pleckstrin homology domain of dynamin 2 cause dominant intermediate Charcot-Marie-Tooth disease. *Nat Genet.* 37(3):289-94 (2005).

Züchner S, Tao F. DNM2-Related Intermediate Charcot-Marie-Tooth Neuropathy. In: Adam M P, Ardinger H H, Pagon R A, Wallace S E, Bean L J H, Stephens K, Amemiya A, editors. GeneReviews® [Internet]. Seattle (Wash.): University of Washington, Seattle; 1993-2018. 2010 Jul. 8 [updated 2015 Jun. 25].

The invention claimed is:

1. A method of treating Charcot-Marie-Tooth disease (CMT), comprising administering an antisense oligonucleotide (AON) capable of inhibiting expression of dynamin 2 to a subject in need thereof, wherein the AON:

comprises a nucleic acid sequence TCAGGCCGCCC-CATTTTACCTGTTT (SEQ ID NO: 3) or a sequence exhibiting at least 90% identity with sequence SEQ ID NO: 3; or targets the region containing 100 nucleotides upstream of the ATG; or comprises a nucleic acid sequence CTGGACCATCC-TATGAGGAAAAGGA (SEQ ID NO: 1) or a sequence exhibiting at least 90% identity with sequence SEQ ID NO: 1; or enables skipping of exon 6 on the dynamin 2 pre-mRNA.

2. The method according to claim 1, wherein the CMT is dominant intermediate CMT (DI-CMTB), axonal CMT (CMT2M), dominant intermediate CMT 1 (CMTDI1), dominant intermediate CMT B (CMTDIB), or CMT type 4B (CMT4B).

3. The method according to claim 1, wherein the AON targets a junction between exon 6 and intron 6 on the dynamin 2 pre-mRNA enabling skipping of exon 6 on the dynamin 2 pre-mRNA.

4. The method according to claim 1, wherein the AON comprises a nucleic acid sequence GACCCTCAACGACCTGGCCCC (SEQ ID NO: 4) or a sequence exhibiting at least 90% identity with sequence SEQ ID NO: 4.

5. The method according to claim 1, wherein the AON comprises a nucleic acid sequence CGTGCAAACCCTTGCAGTACCTGAT (SEQ ID NO: 2) or a sequence exhibiting at least 90% identity with sequence SEQ ID NO: 2.

6. An antisense oligonucleotide (AON), capable of inhibiting expression of dynamin 2, wherein the AON:
   comprises a nucleic acid sequence TCAGGCCGCCCCATTTTACCTGTTT (SEQ ID NO: 3) or a sequence exhibiting at least 90% identity with sequence SEQ ID NO: 3; or
   targets the region containing 100 nucleotides upstream of the ATG; or
   comprises a nucleic acid sequence CTGGACCATCCTATGAGGAAAAGGA (SEQ ID NO: 1) or a sequence exhibiting at least 90% identity with sequence SEQ ID NO: 1; or
   enables skipping of exon 6 on the dynamin 2 pre-mRNA; wherein the AON is in the form of a morpholino oligonucleotide.

7. The antisense oligonucleotide according to claim 6 wherein the AON comprises a nucleic acid sequence GACCCTCAACGACCTGGCCCC (SEQ ID NO: 4) or a sequence exhibiting at least 90% identity with sequence SEQ ID NO: 4.

8. The antisense oligonucleotide according to claim 6 wherein the AON targets the junction between exon 6 and intron 6 on the dynamin 2 pre-mRNA.

9. The antisense oligonucleotide according to claim 6 wherein the AON comprises a nucleic acid sequence CGTGCAAACCCTTGCAGTACCTGAT (SEQ ID NO: 2) or a sequence exhibiting at least 90% identity with sequence SEQ ID NO: 2.

10. A method of treating a centronuclear myopathy (CNM) comprising administering an antisense oligonucleotide (AON) to a subject in need thereof, wherein the AON:
    comprises a nucleic acid sequence TCAGGCCGCCCCATTTTACCTGTTT (SEQ ID NO: 3) or a sequence exhibiting at least 90% identity with sequence SEQ ID NO: 3; or
    targets the region containing 100 nucleotides upstream of the ATG; or
    comprises a nucleic acid sequence CTGGACCATCCTATGAGGAAAAGGA (SEQ ID NO: 1) or a sequence exhibiting at least 90% identity with sequence SEQ ID NO: 1; or
    enables skipping of exon 6 on the dynamin 2 pre-mRNA.

11. A viral vector containing an antisense oligonucleotide (AON), wherein the AON:
    comprises a nucleic acid sequence TCAGGCCGCCCCATTTTACCTGTTT (SEQ ID NO: 3) or a sequence exhibiting at least 90% identity with sequence SEQ ID NO: 3; or
    targets the region containing 100 nucleotides upstream of the ATG; or
    comprises a nucleic acid sequence CTGGACCATCCTATGAGGAAAAGGA (SEQ ID NO: 1) or a sequence exhibiting at least 90% identity with sequence SEQ ID NO: 1; or
    enables skipping of exon 6 on the dynamin 2 pre-mRNA.

12. A pharmaceutical composition comprising the antisense oligonucleotide according to claim 6 or the viral vector of claim 11.

13. The method according to claim 1, further comprising administering myotubularin.

14. A kit comprising the antisense oligonucleotide according to claim 6 or the viral vector of claim 11 and instructions for their use.

* * * * *

SEQUENCE LISTING

```
<160> NUMBER OF SEQ ID NOS: 20

<210> SEQ ID NO 1
<211> LENGTH: 25
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: "human i7e8 splice junction (PMO 4)"

<400> SEQUENCE: 1
ctggaccatc ctatgaggaa aagga                                         25

<210> SEQ ID NO 2
<211> LENGTH: 25
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: "human e6i6 splice junction (PMO 3)"

<400> SEQUENCE: 2
cgtgcaaacc cttgcagtac ctgat                                         25

<210> SEQ ID NO 3
<211> LENGTH: 25
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: "human e2i2 splice junction (PMO 2)"

<400> SEQUENCE: 3
tcaggccgcc ccattttacc tgttt                                         25

<210> SEQ ID NO 4
<211> LENGTH: 21
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: "human 5'UTR (PMO 1)"

<400> SEQUENCE: 4
gaccctcaac gacctggccc c                                             21

<210> SEQ ID NO 5
<211> LENGTH: 25
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: "murine 5' UTR (PMO-A )"

<400> SEQUENCE: 5
cgactaagac tctcggttcc gatgt                                         25

<210> SEQ ID NO 6
```

```
<211> LENGTH: 23
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: "murine 5'UTR (PMO-B)"

<400> SEQUENCE: 6
tcatccggtt ctcaggcgac acc                                         23

<210> SEQ ID NO 7
<211> LENGTH: 25
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: "murine e2i2 splice junction (PMO-C)"

<400> SEQUENCE: 7
ccctgaattt ctatttctca tacct                                       25

<210> SEQ ID NO 8
<211> LENGTH: 25
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: "murine e6i6 splice junction (PMO-D)"

<400> SEQUENCE: 8
ggtggcctca aacctccgct atacc                                       25

<210> SEQ ID NO 9
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: "murine 5' UTR (PMO-E)"

<400> SEQUENCE: 9
ttgcccatgg tgtccgcctc                                             20

<210> SEQ ID NO 10
<211> LENGTH: 21
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: "murine 5' UTR (PMO-F)"

<400> SEQUENCE: 10
ttgcttcctc ctgctctgct c                                           21

<210> SEQ ID NO 11
<211> LENGTH: 25
<212> TYPE: DNA
<213> ORGANISM: Artificial Sequence
<220> FEATURE:
```

```
<223> OTHER INFORMATION: Synthetic Polynucleotide
<220> FEATURE:
<221> NAME/KEY: misc_feature
<223> OTHER INFORMATION: "Sequence cible PMO A"

<400> SEQUENCE: 11
acatcggaac cgagagtctt agtcg                                              25

<210> SEQ ID NO 12
<211> LENGTH: 23
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: "Sequence cible PMO B"

<400> SEQUENCE: 12
ggtgtcgcct gagaaccgga tga                                                23

<210> SEQ ID NO 13
<211> LENGTH: 25
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: "Sequence cible PMO C"

<400> SEQUENCE: 13
aggtatgaga aatagaaatt caggg                                              25

<210> SEQ ID NO 14
<211> LENGTH: 25
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: "Sequence cible PMO D"

<400> SEQUENCE: 14
ggtatagcgg aggtttgagg ccacc                                              25

<210> SEQ ID NO 15
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: "Sequence cible PMO E"

<400> SEQUENCE: 15
gaggcggaca ccatgggcaa                                                    20

<210> SEQ ID NO 16
<211> LENGTH: 21
<212> TYPE: DNA
<213> ORGANISM: Artificial Sequence
<220> FEATURE:
<223> OTHER INFORMATION: Synthetic Polynucleotide
<220> FEATURE:
<223> OTHER INFORMATION: "Sequence cible PMO F"
```

```
<400> SEQUENCE: 16
gagcagagca ggaggaagca a                                          21

<210> SEQ ID NO 17
<211> LENGTH: 21
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: "Sequence cible PMO 1"

<400> SEQUENCE: 17
ggggccaggt cgttgagggt c                                          21

<210> SEQ ID NO 18
<211> LENGTH: 25
<212> TYPE: DNA
<213> ORGANISM: Artificial Sequence
<220> FEATURE:
<223> OTHER INFORMATION: Synthetic Polynucleotide
      220>
<221> NAME/KEY: misc_feature
<223> OTHER INFORMATION: "Sequence cible PMO 2"

<400> SEQUENCE: 18
aaacaggtaa aatggggcgg cctga                                      25

<210> SEQ ID NO 19
<211> LENGTH: 25
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: "Sequence cible PMO 3"

<400> SEQUENCE: 19
atcaggtact gcaagggttt gcacg                                      25

<210> SEQ ID NO 20
<211> LENGTH: 25
<212> TYPE: DNA
<213> ORGANISM: Artificial Sequence
<220> FEATURE:
<223> OTHER INFORMATION: Synthetic Polynucleotide
      220>
<221> NAME/KEY: misc_feature
<223> OTHER INFORMATION: "Sequence cible PMO 4"

<400> SEQUENCE: 20 tcctttttcct cataggatgg tccag                                     25
```